(12) United States Patent
Jain et al.

(10) Patent No.: US 11,377,447 B2
(45) Date of Patent: Jul. 5, 2022

(54) TARGETED THERAPEUTICS

(71) Applicant: MADRIGAL PHARMACEUTICALS, INC., West Conshohocken, PA (US)

(72) Inventors: Neera Jain, Burlington, MA (US); Weiwen Ying, Lexington, MA (US); Dinesh U. Chimmanamada, Arlington, MA (US); Junyi Zhang, Lexington, MA (US); Amit Kale, Stow, MA (US)

(73) Assignee: MADRIGAL PHARMACEUTICALS, INC., West Conshohocken, PA (US)

( * ) Notice: Subject to any disclaimer, the term of this patent is extended or adjusted under 35 U.S.C. 154(b) by 0 days.

(21) Appl. No.: 16/625,349

(22) PCT Filed: Jun. 19, 2018

(86) PCT No.: PCT/US2018/038153
§ 371 (c)(1),
(2) Date: Dec. 20, 2019

(87) PCT Pub. No.: WO2018/236781
PCT Pub. Date: Dec. 27, 2018

(65) Prior Publication Data
US 2020/0239472 A1 Jul. 30, 2020

Related U.S. Application Data

(60) Provisional application No. 62/522,314, filed on Jun. 20, 2017.

(51) Int. Cl.
*C07D 471/14* (2006.01)
*A61K 47/10* (2017.01)

(52) U.S. Cl.
CPC ............ *C07D 471/14* (2013.01); *A61K 47/10* (2013.01)

(58) Field of Classification Search
CPC ............................ C07D 471/14; C07D 491/22
USPC ...................................................... 546/70, 48
See application file for complete search history.

(56) References Cited

U.S. PATENT DOCUMENTS

| | | | |
|---|---|---|---|
| 6,214,345 B1 | 4/2001 | Firestone et al. |
| 6,372,712 B1 | 4/2002 | Briesewitz et al. |
| 7,344,699 B2 | 3/2008 | Lappin et al. |
| 7,671,010 B2 | 3/2010 | Arap et al. |
| 7,769,423 B2 | 8/2010 | Viglianti et al. |
| 7,834,181 B2 | 11/2010 | Chiosis et al. |
| 2002/0147133 A1 | 10/2002 | Briesewitz et al. |
| 2005/0261170 A1 | 11/2005 | Hansen et al. |
| 2007/0134154 A1 | 6/2007 | Chang et al. |
| 2007/0297980 A1 | 12/2007 | Xie et al. |
| 2009/0226431 A1 | 9/2009 | Habib |
| 2009/0298857 A1 | 12/2009 | Chiosis et al. |
| 2011/0064751 A1 | 3/2011 | Mossner et al. |
| 2011/0165699 A1 | 7/2011 | Salamone et al. |
| 2011/0217241 A1 | 9/2011 | Yu et al. |
| 2011/0270151 A1 | 11/2011 | Li |
| 2012/0003160 A1 | 1/2012 | Wolf et al. |
| 2015/0104407 A1 | 4/2015 | Yurkovetskiy et al. |
| 2015/0105539 A1 | 4/2015 | Miao et al. |
| 2015/0105540 A1 | 4/2015 | Miao et al. |
| 2017/0128580 A1 | 5/2017 | Chimmanamada et al. |

FOREIGN PATENT DOCUMENTS

| | | |
|---|---|---|
| CN | 1 995 020 A | 7/2011 |
| EP | 2133094 A1 | 12/2009 |
| JP | 2005-520795 A | 7/2005 |
| JP | 2012-502921 A | 2/2012 |
| JP | 6305981 | 3/2018 |
| WO | 2000/061578 A1 | 10/2000 |
| WO | 2002/036171 A1 | 5/2002 |
| WO | 2003/050295 A1 | 6/2003 |
| WO | 2003/055860 A1 | 7/2003 |
| WO | 2004/054624 A1 | 7/2004 |
| WO | 2005/007136 A1 | 1/2005 |
| WO | 2007/053792 A1 | 5/2007 |
| WO | 2007/077209 A1 | 7/2007 |
| WO | 2008/044029 A1 | 4/2008 |
| WO | 2008/106129 A2 | 4/2008 |
| WO | 2009/036092 A2 | 3/2009 |
| WO | 2010/017545 A2 | 2/2010 |
| WO | 2010/028389 A1 | 3/2010 |
| WO | 2010/033733 A1 | 3/2010 |
| WO | 2011/116181 A1 | 9/2011 |
| WO | 2011/133879 A2 | 10/2011 |
| WO | 2012/052843 A1 | 4/2012 |
| WO | 2012/096919 A1 | 7/2012 |
| WO | 2012/149493 A2 | 11/2012 |
| WO | 2013/028505 A2 | 2/2013 |
| WO | 2013/158644 A2 | 10/2013 |
| WO | 2015/038649 A1 | 3/2015 |
| WO | 2018/236793 A1 | 12/2018 |
| WO | 2019/195386 A1 | 10/2019 |

OTHER PUBLICATIONS

Azark, R. G., et al., "Therapeutic Synergy Between Irinotecan and 5-Fluorouracil against Human Tumor Xenografts" (2004) Clinical Cancer Research 10:1121-1129.

(Continued)

*Primary Examiner* — Charanjit Aulakh
(74) *Attorney, Agent, or Firm* — DT Ward, PC; Donna T. Ward; Heng Zhu

(57) ABSTRACT

The present invention provides pharmacological compounds including an effector moiety conjugated to a binding moiety that directs the effector moiety to a biological target of interest. Likewise, the present invention provides compositions, kits, and methods (e.g., therapeutic, diagnostic, and imaging) including the compounds. The compounds can be described as a protein interacting binding moiety-drug conjugate (SDC-TRAP) compounds, which include a protein interacting binding moiety and an effector moiety. For example, in certain embodiments directed to treating cancer, the SDC-TRAP can include an Hsp90 inhibitor conjugated to a cytotoxic agent as the effector moiety.

1 Claim, 1 Drawing Sheet

(56) References Cited

OTHER PUBLICATIONS

Rowinsky, E.K. et al., "Phase I and Pharmacologic Study of A Novel Topoisomerase I Inhibitor" (1992) Journal of Clinical Oncology 10(4):647-656.

Thomas, D.A. et al., "Phase II Study of Sphingosomal Vincristine in Patients with Recurrent or Refractory Adult Acute Lymphocytic Leukemia" (2006) Cancer 106(1):120-127.

Tsakalozou, E. et al., "An HPLC Assay for the Lipophilic Camptothecin Analog AR-67 Carboxylate and Lactone in Human Whole Blood" (2010) 24(10):1045-1051.

International Search Report and Written Opinion dated Aug. 27, 2018 in corresponding PCT application PCT/ US18/38153, entitled "Targeted Therapeutics".

Arap, W. et al., "Cancer Treatment by Targeted Drug Delivery to Tumor Vasculature in a Mouse Model" (1998) Science 279:377-380.

Bader, R.A., "The Development of Targeted Drug Delivery Systems for Rheumatoid Arthritis Treatment" (2012) Book edited by Andrew B. Lemmey, ISBN 978-953-307-850-2, http://www.intechopen.com/books/rheumatoid-arthritis-treatment.

Baker, J.R., Jr., "Dendrimer-based nanoparticles for cancer therapy" (2009) Hematology pp. 708-719.

Borgman, M.P. et al., "Biodistribution of HPMA Copolymer-Aminohexylgeldanamycin-RGDfK Conjugates for Prostate Cancer Drug Delivery" (2009) Molecular Pharmaceuticals 6(6): 1836-1847.

Borman, S. "Multivalency: Strength in Numbers" (2000) C&EN pp. 48-53.

Burkitt, M. et al. "Potentiation of Chemotherapeutics by the Hsp90 Antagonist Geldanamycin Requires a Steady Serum Condition" (2007) Mol. Carcinog. 46:466-475.

Chen, C. Y.-C., "Bioinformatics, chemoinformatics, and pharmainformatics analysis of HER2/HSP90 dual-targeted inhibitors" (2010) J. Taiwan Chem. Eng. 41:143-149.

Dharap, S.S. et al., "Tumor-specific targeting of an anticancer drug delivery system by LHRH peptide" (2005) PNAS 102(36):12962-12967.

Du, Y. et al., "High-Throughput Screening Fluorescence Polarization Assay for Tumor Specific Hsp90" (2007) J. Biomolecular Screening 12(7):915-924.

Ducry, L. and B. Stump, "Antibody-Drug Conjugates: Linking Cytotoxic Payloads to Monoclonal Antibodies" (2010) Bioconjugate Chem. 21 (1):5-13.

Gerber, D.E., "Targeted Therapies: A New Generation of Cancer Treatments" (2008) American Family Physician 77 (3):311-319.

Graham, B. et al., "The heat shock protein 90 inhibitor, AT13387, displays a long duration of action in vitro and in vivo in non-small cell lung cancer" (2012) Cancer Science 103(3):522-527.

Guo, W. et al., "Enzyme Reduction and Glutathione Conjugation of Benzoquinone Ansamycin Heat Shock Protein 90 Inhibitors: Relevance for Toxicity and Mechanism of Action" (2008) 36(10):2050-2057.

Hatakeyama, S. et al., "Targeted drug delivery to tumor vasculature by a carbohydrate mimetic peptide" (2011) PNAS 108(49):19587-19592.

Howes, R. et al., "A fluorscence polarization assay for inhibitors of Hsp90" (2006) Analytical Biochemistry 350:202-213.

Imai, T. et al. "Heat shock protein 90 (HSP90) contributes to cytosolic translocation of extracellular antigen for cross-presentation by dendritic cells" (2011) PNAS 108(39): 16363-16368.

Inoue, T. et al., "An inducible translocation strategy to rapidly activate and inhibit small GTPase signaling pathways" (2005) Nature Methods 2(2):415-418.

Janáky, T. et al., "Analogues of luteinizing hormone-releasing hormone containing cytotoxic groups" (1992) Proc. Natl. Acad. Sci. 89:972-976.

Jaracz, S. et al., "Recent advances in tumor-targeting anticancer drug conjugates" (2005) Bioorganic & Medicinal Chemistry 13:5043-5054.

Jhaveri, K. et al., "Ganetespib:research and clinical development" (2015) Onco Targets and Therapy 8:1849-1858.

Kagaku, S.S., "The Practice of Medicinal Chemistry First Volume" (2001) First edition, 3rd printing, pp. 297-301 and 318-327.

Kaiser, M. et al., "Synergistic action of the novel HSP90 inhibitor NVP-AUY922 with histone deacetylase inhibitors, melphalan, or doxorubicin in multiple myeloma" (2010) Eur. J. Haematol. 84:337-344.

Kim, Y.-S. et al., "Effects of Targeting Moiety, Linker, Bifunctional Chelator, and Molecular Charge on Biological Properties of 64Cu-Labeled Triphenylphosphonium Cations" (2008) J. Med. Chem. 51:2971-2984.

Koga, F. et al., "Inhibition of Cancer Invasion and Metastasis by Targeting the Molecular Chaperone Heat-shock Protein 90" (2009) Anticancer Research 29:797-808.

Kuduk, S.D., et al., "Synthesis and Evaluation of Geldanamycin-Testosterone Hybrids" (2000) Bioorg. Med. Chem. Letters 10:1303-1306.

Leamon, C.P. and J.A. Reddy, "Folate-targeted chemotherapy" (2004) Advanced Drug Delivery Reviews 56:1127-1141.

Lee, Y.-H., et al., "Antitumor activity of NVP-AUY922, a novel heat shock protein 90 inhibitor, in human gatric cancer cells is mediated through proteaseomal degradation of client proteins" (2011) Cancer Sci. 102(7):1388-1395.

Mandler, R. et al., "Synthesis and Evaluation of Antiproliferative Activity of a Geldanamycin-HerceptinTM Immunoconjugate" (2000) Bioorg. & Med. Chem. Letters 10:1025-1028.

Nagy, A. et al., "Selective coupling of methotrexate to peptide hormone carriers through a γ-carboxamide linkage of its glutamic acid moiety: Benzotriazol-1-yloxytris(dimethylamino)phosphonium hexafluorophosphate activation in salt coupling" (1993) Proc. Natl. Acad. Sci. 90(13):6373-6376.

Norez, C. et al., "Chemical conjugation of F508-CFTR corrector deoxyspergualin to transporter human serum albumin enhances its ability to rescue C1-channel functions" (2008) Am. J. Physiol. Lung Cell Mol. Physiol 295:L336-L347.

Park, D. et al., "Noninvasive Imaging of Cell Death Using an Hsp90 Ligand" (2011) J. Am. Chem. Soc. 133 (9):2832-2835.

Prioa, D.A., "Synergistic activity of the Hsp90 inhibitor ganetespib with taxanes in non-small cell lung cancermodels" (2012) Invest. New Drugs 30:2201-2209.

Rao, R. et al., "Co-treatment with heat shock protein 90 inhibitor 17-dimethylaminoethylamino-17-demethoxygeldanamycin (DMAG) and vorinostat" (2009) Cancer Biology & Therapy 8(13) 1273-1280.

Rigaudy, P. et al., "Attempts to Target Antitumor Drugs toward Opioid Receptor-rich Mouse Tumor Cells with Enkephalin-Ellipticinium Conjugates" (1989) Cancer Research 49(7): 1836-1842.

Rivory, Laurent P., et al. "Conversion of irinotecan (CPT-11) to its active metabolite, 7-ethyl-10-hydroxycamptothecin (SN-38), by human liver carboxylesterase." Biochemical pharmacology52.7 (1996): 1103-1111.

Scarano, W. et al., "Folate Conjugation to Polymeric Micelles via Boronic Acid Ester to Deliver Platinum Drugs to Ovarian Cancer Cell Lines" (2013) Biomacromolecules 14:962-975.

Sidera, K. and E. Patsavoudi, "Extracellular HSP92" (2008) Cell Cycle 7(10):1564-1568.

Sinha, R., "Nanotechnology in cancer therapeutics: bioconjugated nanoparticles for drug delivery" (2006) Mol. Cancer Ther. 5(8):1909-1917.

Sprancmanis, L.A., et al., "Determination of the anticancer drug, 15-deoxyspergualin, in plasma ultrafiltrate by liquid chromatography and precolumn derivatization with naphthalene-2,3-dicarboxaldehyde/cyanide*" (1990) J. Pharma. & Biomed. Analysis 8(2):165-175.

Stangl, S. et al., "In vivo imaging of CT26 mouse tumours by using cmHsp70.1 monoclonal antibody" (2011) 15 (4):874-887.

(56) References Cited

OTHER PUBLICATIONS

Taldon, T. et al., "Synthesis of purine-scaffold fluorscent probes for heat shock protein 90 with use in flow cytometery and fluorescence microscopy" (2011) Bioorganic & Medical Chemistry Letters 21:5347-5352.

Tse, A.N. et al., "A Phase 1 Dose-Escalation Study of Irinotecan in Combination with 17-Allylamino-17-Demethoxygeldanamycin in Patients with Solid Tumors" (2008) Clin. Cancer Res. 14(20) 6704-6711.

Tse, A.N. et al., "90-kDa Heat Shock Protein Inhibition Abrogates the Topoisomerase I Poison-Induced G2/M Checkpoint in p53-Null Tumor cells by depleting Chk1 and Wee1" (2009) Molecular pharmacology 75(1):124-133.

Tsutsumi, S. et al. "A small molecule cell-impermeant Hsp90 antagonist inhibits tumor cell motility and invasion" (2007) Oncogene 27(17):2478-2487.

Wang, Y. et al., "STA-9090, a small-molecule Hsp90 inhibitor for the potential treatment of cancer" (2010) Current Opinion in Investigational Drugs 11(12):1466-1476.

Webb, S. "Back on target" (2013) Nature Biotechnology 31(3):191-193.

Wick, M.C. et al., "In vivo imaging of the effect of LPS on arterial endothelial cells:molecular imaging of heat shock protein 60 expression" (2008) Cell Stress and Chaperones 13:275-285.

Wozniak, M.B., et al., "Vorinostat interferes with the signaling transduction pathway of T-cell receptor and synergizes with phosphoinositide-3 kinase inhibitors in cutaneous T-cell lymphoma" (2010) Haematolocia 95(4) 613-621.

Proia, D.A., et al. "HSP90 Inhibitor-SN-38 Conjugate Strategy for Targeted Delivery of Topoisomerase I Inhibitor to Tumors" (2015) Mol. Cancer Ther. 14(11) 2422-2432.

Extended European Search Report dated Apr. 9, 2021 in corresponding European Application No. 18820943.1 entitled Targeted Therapeutics.

Amann, R.I., et al., "Combination of 16S rRNA-Targeted Oligonucleotide Probes with Flow Cytometry for Analyzing Mixed Microbial Populations" (1990) Applied and Environmental Microbiology 56(6): 1919-1925.

Office Action dated Oct. 12, 2021 in corresponding Israel patent application No. 270932, entitled Targeted Therapeutics.

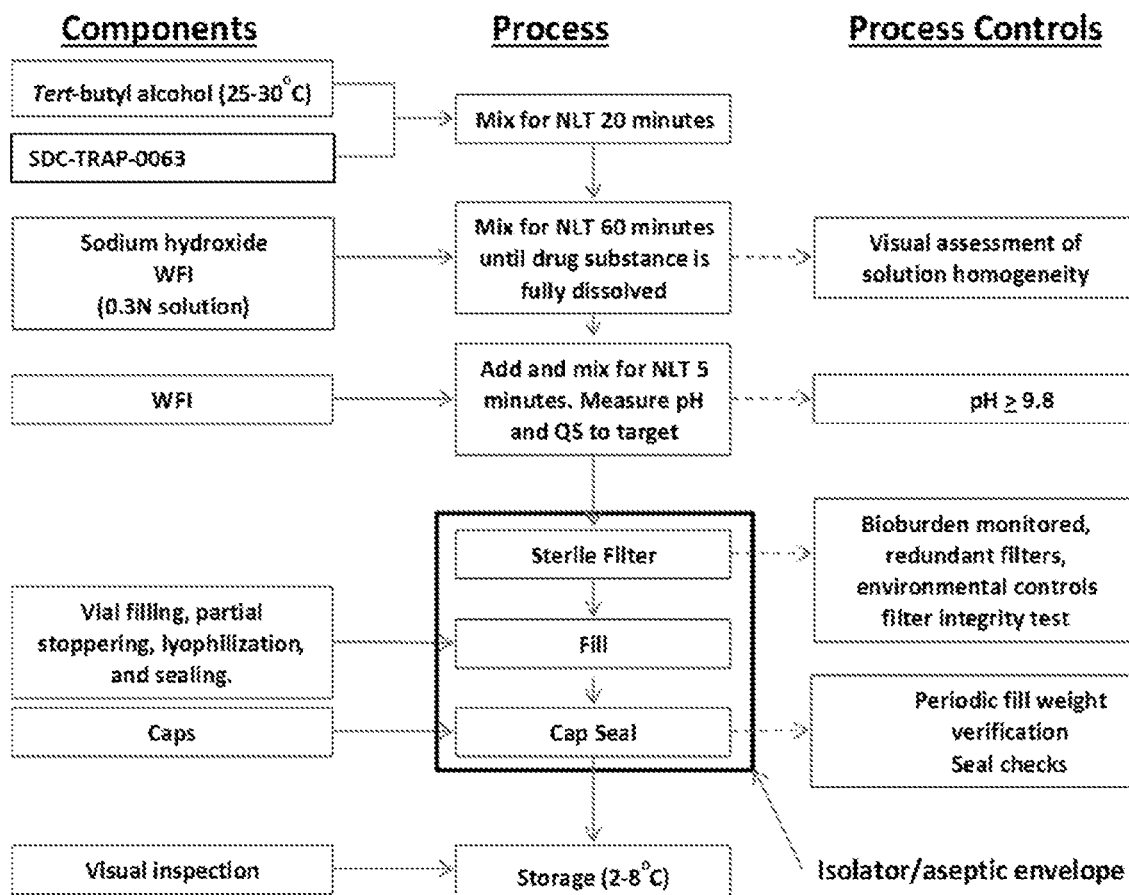

TARGETED THERAPEUTICS

CROSS REFERENCE TO RELATED APPLICATIONS

This application is a 35 U.S.C. § 371 U.S. National Stage Entry of International Application No. PCT/US2018/038153 filed Jun. 19, 2018, entitled "TARGETED THERAPEUTICS", which claims priority to U.S. Provisional Patent Application No. 62/522,314, filed Jun. 20, 2017, entitled "TARGETED THERAPEUTICS", the contents of which are herein incorporated by reference in its entirety.

FIELD OF THE DISCLOSURE

The present invention relates to pharmacological compounds including an effector moiety conjugated to a binding moiety that directs the effector moiety to a biological target of interest. The compounds have broad pharmacological applications, including therapeutics, diagnostics, and imaging. For example, the compounds can specifically direct therapeutic effector moieties to target cells or tissue of interest, for targeted chemotherapeutic treatment of conditions such as cancer.

BACKGROUND

Although tremendous advances have been made in chemotherapy, currently available therapeutics and therapies remain unsatisfactory and the prognosis for the majority of patients diagnosed with chemotherapeutically treated diseases (e.g., cancer) remains poor. Often, the applicability and/or effectiveness of chemotherapy, as well as other therapies and diagnostics employing potentially toxic moieties, is limited by undesired side effects.

Many disease and disorders are characterized by the presence of high levels of certain proteins in specific types of cells. In some cases, the presence of these high levels of protein is caused by overexpression. Historically, some of these proteins have been useful targets for therapeutic molecules or used as biomarkers for the detection of disease. One class of overexpressed intracellular protein that has been recognized as a useful therapeutic target is known as the heat shock proteins.

Heat shock proteins (HSPs) are a class of proteins that are up-regulated in response to elevated temperature and other environmental stresses, such as ultraviolet light, nutrient deprivation, and oxygen deprivation. HSPs have many known functions, including acting as chaperones to other cellular proteins (called client proteins) to facilitate their proper folding and repair, and to aid in the refolding of misfolded client proteins. There are several known families of HSPs, each having its own set of client proteins. Hsp90 is one of the most abundant HSP families, accounting for about 1-2% of proteins in a cell that is not under stress and increasing to about 4-6% in a cell under stress.

Inhibition of Hsp90 results in degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Hsp90 has been shown by mutational analysis to be necessary for the survival of normal eukaryotic cells. However, Hsp90 is overexpressed in many tumor types, indicating that it may play a significant role in the survival of cancer cells and that cancer cells may be more sensitive to inhibition of Hsp90 than normal cells. For example, cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Moreover, inhibition of Hsp90 causes simultaneous inhibition of a number of oncoproteins, as well as hormone receptors and transcription factors, making it an attractive target for an anti-cancer agent. In view of the above, Hsp90 has been an attractive target of drug development, including such Hsp90 inhibitor (Hsp90i) compounds as ganetespib, AUY-922, and IPI-504. At the same time, the advancement of certain of these compounds which showed early promise, e.g., geldanamycin, has been slowed by those compounds' toxicity profile. Hsp90i compounds developed to date are believed to show great promise as cancer drugs, but other ways the ubiquity of Hsp90 in cancer cells might be leveraged have heretofore remained unexplored until now. Accordingly, the need exists for therapeutic molecules that selectively target proteins, such as Hsp90, that are overexpressed in cells associated with particular diseases or disorders.

SUMMARY OF THE DISCLOSURE

The present invention provides pharmacological molecules ("SDC-TRAPs") including an effector moiety conjugated to a binding moiety, which directs the effector moiety into a target cell of interest in a manner that traps the molecule in the target cell. Methods of making and using the SDC-TRAPs are also provided.

The present invention is described in further detail by the figures and examples below, which are used only for illustration purposes and are not limiting.

BRIEF DESCRIPTION OF THE DRAWINGS

FIG. 1 is a flow diagram for the manufacturing processes and process control of SDC-TRAP-0063 Sodium.

Other features and advantages of the instant invention will be apparent from the following detailed description and claims.

DETAILED DESCRIPTION

The present invention provides molecules including an effector moiety conjugated to a binding moiety that directs the effector moiety to a biological target of interest. The molecules of the invention allow for selective targeting of an effector moiety by trapping the molecules of the invention in a desired cell, e.g., a cancer cell. The molecules can be described as Small molecule Drug Congugates that are TRAPped intracellularly (SDC-TRAP), due to their selective binding to high concentration intracellular proteins. In order for the molecules of the invention to be trapped within the cells of interest, the binding moieties that are part of the SDC-TRAP molecules interact with proteins that are overexpressed in targeted cells. In exemplary embodiments, the proteins that are overexpressed are characteristic of a particular disease or disorder. Accordingly, the present invention provides compositions, kits, and methods (e.g., therapeutic, diagnostic, and imaging) that include the molecules of the invention.

In one embodiment of the invention, SDC-TRAPs allow for the delivery of an effector molecule that would otherwise be unsuitable for administration alone due to toxicity and/or undesired systemic effects. Using the targeted delivery molecules described herein (SDC-TRAPs) allows for effector moieties that are too toxic to administer by current methods to be dosed at lower levels thereby allowing the toxic effector to be targeted to specific diseased cells at sub-toxic levels.

In various exemplary aspects and embodiments, the present invention provides compounds for treating cancer. For example, an SDC-TRAP can comprise an Hsp90 binding moiety (i.e., targeting Hsp90, which is overexpressed in cancer cells compared to normal cells) and an effector moiety (e.g., the Hsp90 binding moiety can be an Hsp90 inhibitor that is conjugated to a cytotoxic agent). As indicated above, the invention is exemplified herein in terms of Hsp90-targeted binding moieties and cytotoxic agents. Other binding moieties that are contemplated, mentioned or described herein are intended to be included within the scope of the invention.

In various aspects and embodiments, the present invention provides an SDC-TRAP comprising a binding moiety and an effector moiety, wherein the SDC-TRAP molecule is able to enter a cell by passive transport. The ability of an SDC-TRAP to enter a cell by passive transport can be a result of one or more unique chemical properties of the SDC-TRAP (e.g., size, weight, charge, polarity, hydrophobicity, etc.) and can facilitate the delivery and/or action of the SDC-TRAP. The ability of an SDC-TRAP to enter a cell by passive transport is a functional property, which along with its physico-chemical properties, differentiates SDC-TRAPs from other targeted molecules such as antibody-drug conjugates.

In various aspects and embodiments, the present invention provides an SDC-TRAP comprising a binding moiety and an effector moiety, wherein SDC-TRAP molecule is able to enter a cell by active transport. The ability of an SDC-TRAP to enter a cell by active transport can be a result of one or more unique chemical properties of the SDC-TRAP and can facilitate the delivery and/or action of the SDC-TRAP. Example of SDC-TRAP active transport can include, for example, endocytosis, phagocytosis, pinocytosis, and exocytosis.

In various aspects and embodiments, the present invention provides an SDC-TRAP having a molecular weight of less than about 5000 Daltons (e.g., less than about 5000, 2500, 2000, 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, etc.). Similarly, in various aspects and embodiments, the present invention provides a binding moiety having a molecular weight of less than about 2500 Dalton (e.g., less than about 2500, 2000, 1600, 800, 750, 700, 650, 600, 550, 500, 450, 400, 350, 300, 250, 200, 150, 100, etc.) and/or an effector moiety having a molecular weight of less than about 2500 Dalton (e.g., less than about 2500, 2000, 1600, 800, 750, 700, 650, 600, 550, 500, 450, 400, 350, 300, 250, 200, 150, 100, etc.). The overall molecular weight of an SDC-TRAP, and the individual weights of a binding moiety, effector moiety, and any linking moiety, can affect transport of the SDC-TRAP. In various examples, it has been observed that lower molecular weights can facilitate delivery and/or activity of an SDC-TRAP.

In various aspects and embodiments, the present invention provides an SDC-TRAP comprising an Hsp90 binding moiety and an effector moiety, wherein the Hsp90 binding moiety and the effector moiety are approximately equal in size (e.g., the Hsp90 binding moiety and the effector moiety have less than about a 25, 50, 75, 100, 125, 150, 175, 200, 225, 250, 275, 300, 325, 350, 375, 400, etc. Dalton difference in molecular weight.) In various examples, it has been observed that lower differences in molecular weight can facilitate delivery and/or activity of an SDC-TRAP.

In various aspects and embodiments, the present invention provides an SDC-TRAP comprising a target protein-interacting binding moiety. A target protein-interacting binding moiety can selectively interact with any one or more domains of a target protein. For example, where a target protein is Hsp90, the binding moiety can be an Hsp90 binding moiety that interacts with the N-terminal domain of Hsp90, the C-terminal domain of Hsp90, and/or the middle domain of Hsp90. Selective interaction with any one or more domains of a target protein can advantageously increase specificity and/or increase the concentration of molecular targets within a target tissue and/or cell.

In various aspects and embodiments, the present invention provides an SDC-TRAP comprising a binding moiety having a high affinity for a molecular target (e.g., a $K_d$ of 50, 100, 150, 200, 250, 300, 350, 400 nM or higher). For example, where a binding moiety is an Hsp90 binding moiety, the Hsp90 binding moiety can have a $K_d$ of 50, 100, 150, 200, 250, 300, 350, 400 nM or higher. A binding moiety having a high affinity for a molecular target can advantageously improve targeting and/or increase the resonance time of the SDC-TRAP in a target cell and/or tissue.

In various aspects and embodiments, the present invention provides an SDC-TRAP comprising a binding moiety (e.g., Hsp90 binding moiety) and an effector moiety, wherein when administered to a subject the SDC-TRAP is present at a ratio of about 2:1 in tumor cells compared to plasma. The ratio can be higher, for example, about 5:1, 10:1, 25:1, 50:1, 75:1, 100:1, 150:1, 200:1, 250:1, 300:1, 400:1, 500:1, 600:1, 700:1, 800:1, 900:1, 1000:1, or greater. In various aspects and embodiments, the ratio is at 1, 2, 3, 4, 5, 6, 7, 8, 12, 24, 48, 72, or more hours from administration. The effectiveness of targeting can be reflected in the ratio of SDC-TRAP in a target cell and/or tissue compared to plasma.

In various aspects and embodiments, the present invention provides an SDC-TRAP comprising a binding moiety (e.g., Hsp90 binding moiety) and an effector moiety, wherein the SDC-TRAP is present in target (e.g., cancer) cells for at least 24 hours. The SDC-TRAP can be present in cancer cells for longer, for example, for at least 48, 72, 96, or 120 hours. It can be advantageous for an SDC-TRAP to be present in target cells for longer periods of time to increase the therapeutic effect of a given dose of SDC-TRAP and/or increase an interval between administrations of SDC-TRAP.

In various aspects and embodiments, the present invention provides an SDC-TRAP comprising a binding moiety (e.g., Hsp90 binding moiety) and an effector moiety, wherein the effector moiety is released for a period of at least 6 hours. The effector moiety can be released for a longer period, for example, for at least 12, 24, 48, 72, 96, or 120 hours. Selective release can be used to control, delay, and/or extend the period of release of an effector moiety and, therefore, increase the therapeutic effect of a given dose of SDC-TRAP, decrease the undesired side effects of a given dose of SDC-TRAP, and/or increase an interval between administrations of SDC-TRAP.

In various aspects and embodiments, the present invention provides an SDC-TRAP comprising an Hsp90 binding moiety and an effector moiety, wherein the effector moiety is selectively released inside a target (e.g., cancer) cell. Selective release can be achieved, for example, by a cleavable linker (e.g., an enzymatically cleavable linker). Selective release can be used to decrease undesired toxicity and/or unwanted side effects. For example, an SDC-TRAP can be designed where an effector moiety such is inactive (or relatively inactive) in a conjugated form, but active (or more active) after it is selectively released inside a target (e.g., cancer) cell.

In various aspects and embodiments, the present invention provides an SDC-TRAP comprising a binding moiety (e.g., Hsp90 binding moiety) and an effector moiety, wherein the SDC-TRAP allows for the use of an effector moiety that is otherwise toxic or unfit for administration to a subject. The effector moiety can be unfit for administration to a subject because of undesired toxicity. In such cases, a strategy such as selective release may be used to address the undesired toxicity. The effector moiety can be unfit for administration to a subject because of undesired targeting or a lack of targeting. Targeting can address such problems, for example, by minimizing systemic toxicity while maximizing local toxicity at a target (e.g., a tumor).

In various aspects and embodiments, the present invention provides an SDC-TRAP comprising a binding moiety (e.g., Hsp90 binding moiety) and an effector moiety, wherein the binding moiety is an inhibitor (e.g., Hsp90 inhibitor) that is ineffective as a therapeutic agent when administered alone. In such cases, the SDC-TRAP may facilitate an additive or synergistic effect between the binding moiety and effector moiety, thereby advantageously improving the efficacy and/or reducing the side effects of a therapy.

In order that the present invention may be more readily understood, certain terms are first defined. In addition, it should be noted that whenever a value or range of values of a parameter are recited, it is intended that values and ranges intermediate to the recited values are also intended to be part of this invention. Unless defined otherwise, all technical and scientific terms used herein have the same meaning as commonly understood to one of ordinary skill in the art to which this invention belongs. It is also to be understood that the terminology employed is for the purpose of describing particular embodiments, and is not intended to be limiting.

Definitions

The articles "a," "an," and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to."

The term "or" is used herein to mean, and is used interchangeably with, the term "and/or," unless context clearly indicates otherwise.

The term "such as" is used herein to mean, and is used interchangeably, with the phrase "such as but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment. Treatment does not need to be curative.

A "therapeutically effective amount" is that amount sufficient to treat a disease in a subject. A therapeutically effective amount can be administered in one or more administrations.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

The terms "administer," "administering" or "administration" include any method of delivery of a pharmaceutical composition or agent into a subject's system or to a particular region in or on a subject. In certain embodiments of the invention, an agent is administered intravenously, intramuscularly, subcutaneously, intradermally, intranasally, orally, transcutaneously, or mucosally. In a preferred embodiment, an agent is administered intravenously. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, the term "recur" refers to the re-growth of tumor or cancerous cells in a subject in whom primary treatment for the tumor has been administered. The tumor may recur in the original site or in another part of the body. In one embodiment, a tumor that recurs is of the same type as the original tumor for which the subject was treated. For example, if a subject had an ovarian cancer tumor, was treated and subsequently developed another ovarian cancer tumor, the tumor has recurred. In addition, a cancer can recur in or metastasize to a different organ or tissue than the one where it originally occurred.

As used herein, the terms "identify" or "select" refer to a choice in preference to another. In other words, to identify a subject or select a subject is to perform the active step of picking out that particular subject from a group and confirming the identity of the subject by name or other distinguishing feature.

As used herein, the term "benefit" refers to something that is advantageous or good, or an advantage. Similarly, the term "benefiting," as used herein, refers to something that improves or advantages. For example, a subject will benefit from treatment if they exhibit a decrease in at least one sign or symptom of a disease or condition (e.g., tumor shrinkage, decrease in tumor burden, inhibition or decrease of metastasis, improving quality of life ("OOL"), if there is a delay of time to progression ("TTP"), if there is an increase of overall survival ("OS"), etc.), or if there is a slowing or stopping of disease progression (e.g., halting tumor growth or metastasis, or slowing the rate of tumor growth or metastasis). A benefit can also include an improvement in quality of life, or an increase in survival time or progression free survival.

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features. Cancer cells are often in the form of a solid tumor. However, cancer also includes non-solid tumors, e.g., blood tumors, e.g., leukemia, wherein the cancer cells are derived from bone marrow. As used herein, the term "cancer" includes pre-malignant as well as malignant cancers. Cancers include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, Burkitt's lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin, and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor. Other cancers include primary cancer, metastatic cancer, oropharyngeal cancer, hypopharyngeal cancer, liver cancer, gall bladder cancer, bile duct cancer, small intestine cancer, urinary tract cancer, kidney cancer, urothelium cancer, female genital tract cancer, uterine cancer, gestational trophoblastic disease, male genital tract cancer, seminal vesicle cancer, testicular cancer, germ cell tumors, endocrine gland tumors, thyroid cancer, adrenal cancer, pituitary gland cancer, hemangioma, sarcoma arising from bone and soft tissues, Kaposi's sarcoma, nerve cancer, ocular cancer, meningial cancer, glioblastomas, neuromas, neuroblastomas, Schwannomas, solid tumors arising from hematopoietic malignancies such as leukemias, metastatic melanoma, recurrent or persistent ovarian epithelial cancer, fallopian tube cancer, primary peritoneal cancer, gastrointestinal stromal tumors, colorectal cancer, gastric cancer, melanoma, glioblastoma multiforme, non-squamous non-small-cell lung cancer, malignant glioma, epithelial ovarian cancer, primary peritoneal serous cancer, metastatic liver cancer, neuroendocrine carcinoma, refractory malignancy, triple negative breast cancer, HER2-amplified breast cancer, nasopharageal cancer, oral cancer, biliary tract, hepatocellular carcinoma, squamous cell carcinomas of the head and neck (SCCHN), non-medullary thyroid carcinoma, recurrent glioblastoma multiforme, neurofibromatosis type 1, CNS cancer, liposarcoma, leiomyosarcoma, salivary gland cancer, mucosal melanoma, acral/lentiginous melanoma, paraganglioma, pheochromocytoma, advanced metastatic cancer, solid tumor, triple negative breast cancer, colorectal cancer, sarcoma, melanoma, renal carcinoma, endometrial cancer, thyroid cancer, rhabdomysarcoma, multiple myeloma, ovarian cancer, glioblastoma, gastrointestinal stromal tumor, mantle cell lymphoma, and refractory malignancy.

"Solid tumor," as used herein, is understood as any pathogenic tumor that can be palpated or detected using imaging methods as an abnormal growth having three dimensions. A solid tumor is differentiated from a blood tumor such as leukemia. However, cells of a blood tumor are derived from bone marrow; therefore, the tissue producing the cancer cells is a solid tissue that can be hypoxic.

"Tumor tissue" is understood as cells, extracellular matrix, and other naturally occurring components associated with the solid tumor.

As used herein, the term "isolated" refers to a preparation that is substantially free (e.g., 50%, 60%, 70%, 80%, 90% or more, by weight) from other proteins, nucleic acids, or compounds associated with the tissue from which the preparation is obtained.

The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In one embodiment, the sample is removed from the subject. In a particular embodiment, the sample is urine or serum. In another embodiment, the sample does not include ascites or is not an ascites sample. In another embodiment, the sample does not include peritoneal fluid or is not peritoneal fluid. In one embodiment, the sample comprises cells. In another embodiment, the sample does not comprise cells. Samples are typically removed from the subject prior to analysis. However, tumor samples can be analyzed in the subject, for example, using imaging or other detection methods.

The term "control sample," as used herein, refers to any clinically relevant comparative sample, including, for example, a sample from a healthy subject not afflicted with cancer, a sample from a subject having a less severe or slower progressing cancer than the subject to be assessed, a sample from a subject having some other type of cancer or disease, a sample from a subject prior to treatment, a sample of non-diseased tissue (e.g., non-tumor tissue), a sample from the same origin and close to the tumor site, and the like. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample could be a sample taken from the subject to be assessed before the onset of the cancer, at an earlier stage of disease, or before the administration of treatment or of a portion of treatment. The control sample may also be a sample from an animal model, or from a tissue or cell lines derived from the animal model, of the cancer. The level in a control sample that consists of a group of measurements may be determined, e.g., based on any appropriate statistical measure, such as, for example, measures of central tendency including average, median, or modal values.

As used herein, the term "obtaining" is understood herein as manufacturing, purchasing, or otherwise coming into possession of.

As used herein, the term "identical" or "identity" is used herein in relation to amino acid or nucleic acid sequences refers to any gene or protein sequence that bears at least 30% identity, more preferably 40%, 50%, 60%, 70%, 75%, 80%, 81%, 82%, 83%, 84%, 85%, 86%, 87%, 88%, 89%, 90%, 91%, 92%, 93%, 94%, and most preferably 95%, 96%, 97%, 98%, 99% or more identity to a known gene or protein sequence over the length of the comparison sequence. Protein or nucleic acid sequences with high levels of identity throughout the sequence can be said to be homologous. A "homologous" protein can also have at least one biological activity of the comparison protein. In general, for proteins, the length of comparison sequences will be at least 10 amino acids, preferably 10, 20, 30, 40, 50, 60, 70, 80, 90, 100, 150, 175, 200, 250, or at least 300 amino acids or more. For nucleic acids, the length of comparison sequences will generally be at least 25, 50, 100, 125, 150, 200, 250, 300, 350, 400, 450, 500, 550, 600, 650, 700, 800, or at least 850 nucleotides or more.

As used herein, "detecting," "detection" and the like are understood that an assay performed for identification of a specific analyte in a sample. The amount of analyte or activity detected in the sample can be none or below the level of detection of the assay or method.

The terms "modulate" or "modulation" refer to upregulation (i.e., activation or stimulation), downregulation (i.e., inhibition or suppression) of a level, or the two in combination or apart. A "modulator" is a compound or molecule that modulates, and may be, e.g., an agonist, antagonist, activator, stimulator, suppressor, or inhibitor.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

As used herein, "level of activity" is understood as the amount of protein activity, typically enzymatic activity, as determined by a quantitative, semi-quantitative, or qualitative assay. Activity is typically determined by monitoring the amount of product produced in an assay using a substrate that produces a readily detectable product, e.g., colored product, fluorescent product, or radioactive product.

As used herein, "changed as compared to a control" sample or subject is understood as having a level of the analyte or diagnostic or therapeutic indicator (e.g., marker) to be detected at a level that is statistically different than a sample from a normal, untreated, or control sample control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection the amount and measurement of the change can vary. Changed as compared to a control reference sample can also include a change in one or more signs or symptoms associated with or diagnostic of disease, e.g., cancer. Determination of statistical significance is within the ability of those skilled in the art, e.g., the number of standard deviations from the mean that constitute a positive result.

"Elevated" or "lower" refers to a patient's value of a marker relative to the upper limit of normal ("ULN") or the lower limit of normal ("LLN") which are based on historical normal control samples. As the level of the marker present in the subject will be a result of the disease, and not a result of treatment, typically a control sample obtained from the patient prior to onset of the disease will not likely be available. Because different labs may have different absolute results, values are presented relative to that lab's upper limit of normal value (ULN).

The "normal" level of expression of a marker is the level of expression of the marker in cells of a subject or patient not afflicted with cancer. In one embodiment, a "normal" level of expression refers to the level of expression of the marker under normoxic conditions.

An "over-expression" or "high level of expression" of a marker refers to an expression level in a test sample that is greater than the standard error of the assay employed to assess expression, and is preferably at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 4, 5, 6, 7, 8, 9, or 10 times the expression level of the marker in a control sample (e.g., sample from a healthy subject not having the marker associated disease, i.e., cancer). In one embodiment, expression of a marker is compared to an average expression level of the marker in several control samples.

A "low level of expression" or "under-expression" of a marker refers to an expression level in a test sample that is less than at least 0.9, 0.8, 0.7, 0.6, 0.5, 0.4, 0.3, 0.2, or 0.1 times the expression level of the marker in a control sample (e.g., sample from a healthy subject not having the marker associated disease, i.e., cancer). In one embodiment, expression of a marker is compared to an average expression level of the marker in several control samples.

As used herein, "binding" is understood as having at least a $10^2$ or more, $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody).

"Determining" as used herein is understood as performing an assay or using a diagnostic method to ascertain the state of someone or something, e.g., the presence, absence, level, or degree of a certain condition, biomarker, disease state, or physiological condition.

"Prescribing" as used herein is understood as indicating a specific agent or agents for administration to a subject.

As used herein, the terms "respond" or "response" are understood as having a positive response to treatment with a therapeutic agent, wherein a positive response is understood as having a decrease in at least one sign or symptom of a disease or condition (e.g., tumor shrinkage, decrease in tumor burden, inhibition or decrease of metastasis, improving quality of life ("QOL"), delay of time to progression ("TTP"), increase of overall survival ("OS"), etc.), or slowing or stopping of disease progression (e.g., halting tumor growth or metastasis, or slowing the rate of tumor growth or metastasis). A response can also include an improvement in quality of life, or an increase in survival time or progression free survival.

The terms "administer," "administering" or "administration" can include any method of delivery of a pharmaceutical composition or agent into a subject's system or to a particular region in or on a subject. In certain embodiments of the invention, an Hsp90 inhibitor is administered intravenously, intramuscularly, subcutaneously, intradermally, intranasally, orally, transcutaneously, or mucosally. In a preferred embodiment, an agent is administered intravenously. Administering can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "high concentration" refers to the concentration of SDC-TRAP that accumulates in target cells of the invention due to the selective binding of the binding moiety of the SDC-TRAP to the target protein. In one embodiment, the concentration is higher than in similar cells that do not overexpress the target protein, e.g., lung cancer cells as compared to non-cancerous lung cells. In another embodiment, the concentration is higher in target cells compared to cells that do not express, or overexpress, the target protein. In exemplary embodiments, the high concentration is 1.5, 2, 3, 4, 5, 10, 15, 20, 50, 100, 1000 times or more than cells that are not targeted by the SDC-TRAP molecules of the invention.

The term "moiety" refers generally to a portion of a molecule, which may be a functional group, a set of functional groups, and/or a specific group of atoms within a molecule, that is responsible for a characteristic chemical, biological, and/or medicinal property of the molecule.

The term "binding moiety" refers to low molecular weight (e.g., less than about 2500, 200, 1600, 800, 700, 600, 500, 400, 300, 200, or 100 etc. Dalton) organic compounds, which may serve as a therapeutic or a regulator of a biological process. Binding moieties include molecules that can bind to a biopolymer such as protein, nucleic acid, or polysaccharide and acts as an effector, altering the activity or function of the biopolymer. Binding moieties can have a variety of biological functions, serving as cell signaling molecules, as tools in molecular biology, as drugs in medicine, as pesticides in farming, and in many other roles. These compounds can be natural (such as secondary metabolites) or artificial (such as antiviral drugs); they may have a beneficial effect against a disease (such as drugs) or may be detrimental (such as teratogens and carcinogens). Biopolymers such as nucleic acids, proteins, and polysaccharides (such as starch or cellulose) are not binding moieties, although their constituent monomers—ribo- or deoxyribonucleotides, amino acids, and monosaccharides, respectively—are often considered to be. Small oligomers are also usually considered binding moieties, such as dinucleotides, peptides such as the antioxidant glutathione, and disaccharides such as sucrose.

As used herein, a "protein interacting binding moiety" or "binding moiety" refers to a binding moiety, or portion thereof, that interacts with a predetermined target. The interaction is achieved through some degree of specificity and/or affinity for the target. Both specificity and affinity is generally desirable, although in certain cases higher specificity may compensate for lower affinity and higher affinity may compensate for lower specificity. Affinity and specificity requirements will vary depending upon various factors including, but not limited to, absolute concentration of the target, relative concentration of the target (e.g., in cancer vs. normal cells), potency and toxicity, route of administration, and/or diffusion or transport into a target cell. The target can be a molecule of interest and/or localized in an area of interest. For example, the target can be a therapeutic target and/or localized in an area targeted for a therapy (e.g., a protein that is overexpressed in cancerous cells, as compared to normal cells). In one particular example, a target can be a chaperonin protein such as Hsp90 and the binding moiety can be an Hsp90 binding moiety (e.g., therapeutic, cytotoxic, or imaging moiety). Preferentially, the binding moiety will enhance, be compatible with, or not substantially reduce, passive transport of a conjugate including the binding moiety into a cell, e.g., a cell comprising a target protein.

The term "effector moiety" refers to a molecule, or portion thereof, that has an effect on a target and/or proximally to the target. In various preferred embodiments, the effector moiety is a binding moiety, or portion thereof. An effect can include, but is not limited to, a therapeutic effect, an imaging effect, and/or a cytotoxic effect. At a molecular or cellular level, an effect can include, but is not limited to, promotion or inhibition of the target's activity, labeling of the target, and/or cell death. Preferentially, the effector moiety will enhance, be compatible with, or not substantially reduce, passive transport of a conjugate including the effector moiety into a cell comprising a target. Different effector moieties can be used together and therapeutics in accordance with the present invention may include more than one effector moiety (e.g., two or more different (or same) effector moieties in a single therapeutic in accordance with the present invention, two or more different therapeutics in accordance with the present invention including different effector moieties).

In some embodiments, the effector moiety is selected from the group consisting of peptidyl-prolyl isomerase ligands; rapamycin, cyclosporin A; steroid hormone receptor ligands, antimitotic agents, actin binding agents, camptothecins, topotecan, combretastatins, capecitabine, gemcitabine, vinca alkaloids, platinum-containing compounds, metformin, HDAC inhibitors, thymidylate synthase inhibitors; nitrogen mustards; 5-fluorouracil (5-FU) and its derivatives, or a combination thereof.

In some embodiments, the effector moiety is selected from the group consisting of FK506; rapamycin, cyclosporin A, estrogen, progestin, testosterone, taxanes, colchicine, colcemid, nocadozole, vinblastine, vincristine, cytochalasin, latrunculin, phalloidin, lenalidomide, pomalidomide, SN-38, topotecan, combretastatins, capecitabine, gemcitabine, vinca alkaloids, metformin, suberoylanilidehydroxamic acid (SAHA), methotrexate, pemetrexed, raltitrexed, bendamustine, melphalan; 5-fluorouracil (5-FU), vedotin and DM1, or a combination thereof.

The term "small molecule drug conjugate that is trapped intracellularly" or "binding moiety drug conjugate that is trapped intracellularly" or "SDC-TRAP" refers to a binding moiety and effector moiety joined to one another, or acting as if joined to one another. A binding moiety and effector moiety can be joined through essentially any chemical or physical force, either directly (e.g., binding moiety and effector moiety viewed as two moieties on the same molecule, or a single moiety having both functions) or through an intermediate (e.g., linker). For example, a binding moiety and effector moiety can be joined by one or more covalent bonds, ionic bonds, hydrogen bonds, the hydrophobic effect, dipole-dipole forces, ion-dipole forces, dipole-induced dipole forces, instantaneous dipole-induced dipole forces, and/or combinations thereof. Preferentially, the SDC-TRAP will be capable of passive and/or active transport into a cell comprising a target. Moreover, SDC-TRAP molecules of the invention may comprise multiple effector molecules conjugated to the binding moiety.

The term "linker" or "linking moiety," as used herein in the context of binding moiety, effector moieties, and/or SDC-TRAPs refers to a chemical moiety that joins two other moieties (e.g., a binding moiety and an effector moiety). A linker can covalently join a binding moiety and an effector moiety. A linker can include a cleavable linker, for example an enzymatically cleavable linker. A linker can include a disulfide, carbamate, amide, ester, and/or ether linkers.

As used herein, a "ligand" is a substance (e.g., a binding moiety) that can form a complex with a biomolecule. The ligand and/or formation of the ligand-biomolecule complex can have a biological or chemical effect, such as a therapeutic effect, cytotoxic effect, and/or imaging effect.

As used herein, a "prodrug" is a pharmacological substance that is administered in an inactive or less than fully active form and that is subsequently converted to an active pharmacological agent (i.e., the drug) through a metabolic processes. Prodrugs can be used to improve how the intended drug is absorbed, distributed, metabolized, and/or excreted. A prodrug may also be used to improve how selectively the intended drug interacts with cells or processes that are not its intended target (e.g., to reduce adverse or unintended effects of the intended drug, for example a chemotherapy drug).

The phrase "Hsp90 ligand or a prodrug thereof" refers generally to molecules that bind to and in some cases effect Hsp90, and inactive forms (i.e., prodrugs) thereof. An Hsp90 ligand can be an "Hsp90 inhibitor," which is understood as a therapeutic agent that reduces the activity of Hsp90 either by directly interacting with Hsp90 or by, for example, preventing the formation of the Hsp90/CDC37 complex such that the expression and proper folding of at least one client protein of Hsp90 is inhibited. "Hsp90" includes each member of the family of heat shock proteins having a mass of about 90-kilodaltons. For example, in humans the highly conserved Hsp90 family includes cytosolic Hsp90$^{\alpha}$ and Hsp90$^{\beta}$ isoforms, as well as GRP94, which is found in the endoplasmic reticulum, and HSP75/TRAP1, which is found in the mitochondrial matrix. As used herein, Hsp90 inhibitors include, but are not limited to ganetespib, geldanamycin (tanespimycin), e.g., IPI-493, macbecins, tripterins, tanespimycins, e.g., 17-AAG (alvespimycin), KF-55823, radicicols, KF-58333, KF-58332, 17-DMAG, IPI-504, BIIB-021, BIIB-028, PU-H64, PU-H71, PU-DZ8, PU-HZ151, SNX-2112, SNX-2321, SNX-5422, SNX-7081, SNX-8891, SNX-0723, SAR-567530, ABI-287, ABI-328, AT-13387, NSC-113497, PF-3823863, PF-4470296, EC-102, EC-154, ARQ-250-RP, BC-274, VER-50589, KW-2478, BHI-001, AUY-922, EMD-614684, EMD-683671, XL-888, VER-51047, KOS-2484, KOS-2539, CUDC-305, MPC-3100, CH-5164840, PU-DZ13, PU-HZ151, PU-DZ13, VER-82576, VER-82160, VER-82576, VER-82160, NXD-30001, NVP-HSP990, SST-0201CL1, SST-0115AA1, SST-0221AA1, SST-0223AA1, novobiocin (a C-terminal Hsp90i, herbinmycin A, radicicol, CCT018059, PU-H71, or celastrol.

The term "therapeutic moiety" refers to molecule, compound, or fragment thereof that is used for the treatment of a disease or for improving the well-being of an organism or that otherwise exhibit healing power (e.g., pharmaceuticals, drugs, and the like). A therapeutic moiety can be a chemical, or fragment thereof, of natural or synthetic origin used for its specific action against disease, for example cancer. Therapeutic agents used for treating cancer may be called chemotherapeutic agents. As described herein, a therapeutic moiety is preferentially a small molecule. Exemplary small molecule therapeutics include those that are less than 800 Daltons, 700 Daltons, 600 Daltons, 500 Daltons, 400 Daltons, or 300 Daltons.

The term "cytotoxic moiety" refers to molecule, compound, or fragment thereof that has a toxic or poisonous effect on cells, or that kills cells. Chemotherapy and radiotherapy are forms of cytotoxic therapy. Treating cells with a cytotoxic moiety can produce a variety of results—cells may undergo necrosis, stop actively growing and dividing, or activate a genetic program of controlled cell death (i.e., apoptosis). Examples of cytotoxic moieties include, but are not limited to, SN-38, bendamustine, VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or fragment(s) thereof.

The term "imaging moiety" refers to a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

"Pharmaceutical conjugate" refers to a non-naturally occurring molecule that includes a binding moiety (e.g., an Hsp90-targeting moiety) associated with an effector moiety, where these two components may also be covalently bonded to each other either directly or through a linking group.

The term "drug" refers to any active agent that affects any biological process. Active agents that are considered drugs for purposes of this application are agents that exhibit a pharmacological activity. Examples of drugs include active agents that are used in the prevention, diagnosis, alleviation, treatment or cure of a disease condition.

By "pharmacologic activity" is meant an activity that modulates or alters a biological process so as to result in a phenotypic change, e.g., cell death, cell proliferation etc.

By "pharmacokinetic property" is meant a parameter that describes the disposition of an active agent in an organism or host.

By "half-life" is meant the time for one-half of an administered drug to be eliminated through biological processes, e.g., metabolism, excretion, etc.

The term "efficacy" refers to the effectiveness of a particular active agent for its intended purpose, i.e., the ability of a given active agent to cause its desired pharmacologic effect.

Binding Moiety-Effector Moiety Drug Conjugates that are Trapped Intracellularly (SDC-TRAPs)

The present invention provides SDC-TRAPs, as well as SDC-TRAP compositions, kits, and methods of use thereof. SDC-TRAPs include a binding moiety (e.g., a binding moiety such as a ligand) conjugated to an effector moiety (e.g., a pharmacological agent such as a drug or imaging agent). These two moieties can be joined by a linker, e.g., a covalently-bonded linking group. SDC-TRAPs are useful in a variety of therapeutic, imaging, diagnostic, and/or research applications. In one illustrative example of cancer therapy, an SDC-TRAP can be a pharmaceutical conjugate of an Hsp90-binding moiety such as an Hsp90 ligand or inhibitor associated with an effector moiety such as a therapeutic or cytotoxic agent.

In various embodiments, an SDC-TRAP can be further characterized in that the binding moiety (e.g., targeting moiety) and effector moiety are different, such that the pharmaceutical conjugate may be viewed as a heterodimeric compound produced by the joining of two different moieties. In terms of function, SDC-TRAP molecules have a targeting functionality and effector functionality (e.g., therapeutic, imaging, diagnostic). These functions are provided by corresponding chemical moieties that can be different (or, in some cases, the same). SDC-TRAPs can include any one or more binding moieties conjugated to any one or more effector moieties. In some embodiments, a composition or method can include a combination of two or more binding moeities and/or two or more effector moieties (e.g., a combination therapy and/or multi target therapy) embodied in one or more different types of SDC-TRAPs.

In various embodiments, an SDC-TRAP is further characterized by its ability to passively diffuse and/or be actively transported into a target cell of interest. The diffusion and/or transport properties of the SDC-TRAP can be derived, at least in part, from ionic, polar, and/or hydrophobic properties of the SDC-TRAP. In preferred embodiments, the SDC-TRAP enter cells primarily by passive diffusion. The diffusion and/or transport properties of the SDC-TRAP can be derived, at least in part, from the molecular weight of the SDC-TRAP, the binding moiety, the effector moiety, and/or the similarity in weight between the binding moiety and the effector moiety. SDC-TRAPs are desirably small, such as in comparison to antibody-drug conjugates ("ADCs"). For example, the molecular weight of an SDC-TRAP can be less than about 5000, 2500, 2000, 1600, 1500, 1400, 1300, 1200, 1100, 1000, 900, 800, 700, 600, 500, or 400 Daltons. A binding moiety and an effector moiety can each be less than about 1000, 900, 800, 700, 600, 500, 400, 300, or 200 Daltons. A binding moiety and an effector moiety can be approximately equal in size (e.g., differ in weight by less than 400, 350, 300, 250, 200, 150, 100, or 50 Daltons).

Delivery of an effector molecule by an SDC-TRAP can result in greater potency compared to administering an untargeted drug comprising the same effector moiety, for example, because the SDC-TRAP can be localized at a desired target for an extended period of time through the association of a binding moiety and its target. Such localization can cause an effector moiety to be active and/or released in a target cell and/or tissue over an extended period of time. This resonance time can be selected through deliberate design of a linker moiety. In contrast, administration of the drug by itself in vivo can be more apt to have a shorter resonance time in a given target cell and/or tissue—if it traverses into the cell at all—due to the lack of an "anchor" within the cell.

SDC-TRAPs, in part because they comprise a targeting moiety and are relatively small in size, can be efficiently taken up or internalized by a target cell. Conversely, uptake or internalization is relatively inefficient for ADCs, which must deal with limited antigen expression and relatively inefficient internalization mechanisms for the antibody portion of the molecule. Hsp90 provides a good illustrative example of a difference between SDC-TRAPs and conventional ADCs. By way of comparison, the localization rate of radiolabeled monoclonal antibodies at a tumor in patients is low, on the order of 0.003-0.08% of the injected dose/g tumor. In contrast, a much higher accumulation rate (15-20% injected dose/g tumor) has been measured for SDC-TRAPs in mouse tumor xenografts.

SDC-TRAP pharmaceutical conjugates in accordance with the present invention can represent a significant advance over the state of the art in targeted drugs. SDC-TRAPs have broad application in many therapeutic, imaging, and diagnostic application. As discussed above, SDC-TRAPs are advantageously small in comparison to ADCs, enabling better penetration of solid tumors and more rapid clearance from normal tissues (e.g., reduced toxicity). The design of SDC-TRAPs (e.g., a structure-property relationship) can be established using methods and rationales within the grasp of those of ordinary skill in the art, and companion imaging diagnostics for targeted therapies may also easily be provided, in view of the simpler chemistry involved.

SDC-TRAPs of the invention are characterized by selective targeting of SDC-TRAPs to target cells in which a target protein is overexpressed. This leads to high intracellular concentrations of SDC-TRAP molecules in target cells as compared to non-targeted cells. Likewise, SDC-TRAPs of the invention are characterized by low concentrations of SDC-TRAP in non-targeted cells.

One illustrative embodiment involves a conjugate of an Hsp90 binding moiety linked to a chelator (i.e., the effector moiety, for metals such as In or Gd, which conjugate may function as an imaging agent for the cells/tissues targeted by the conjugate). Another, illustrative embodiment involves a conjugate of an Hsp90 binding moiety linked to a chemotherapeutic (i.e., the effector moiety, for example, SN-38). Alternatively, an illustrative SDC-TRAP is contemplated wherein an Hsp90 targeting moiety bearing radiolabeled halogen (e.g., such as an iodine isotope) can serve to image the cells/tissues targeted by the conjugate, and the effector moiety can be drug to treat the targeted cells/tissues. The progression of treatment may therefore be determined by imaging the tissues being treated and reviewing the images for the presence or absence of the labeled conjugate. Such embodiments are readily adaptable to essentially any cancer, or other chemotherapeutic target. Molecular targets (e.g., interacting with a binding moiety) used to target a particular cell or tissue can be selected based upon their presence in the target cell or tissue and/or their relative abundance in the target cell or tissue (e.g., disease-related versus normal cells).

SDC-TRAP molecules of the present invention represent a new class of drugs. One particular advantage of SDC-TRAPs is that they can be designed to selectively deliver an effector moiety (e.g., a chemotherapeutic drug) into a targeted cell because of the relative overexpression or presence of a binding moiety's molecular target in the cell. After the binding moiety binds the molecular target, the effector moiety is thereafter available (e.g., through cleavage of a linker moiety joining the binding moiety and the effector moiety) to act upon the cell. Accordingly, SDC-TRAPs employ a different mechanism from strategies currently used in the art, for example delivering an Hsp90 inhibitor to a cell using HPMA copolymer-Hsp90i conjugates, Hsp90i prodrugs, nanoparticle-Hsp90i conjugates, or micellar methodologies.

SDC-TRAPs can also be described by the formula:

Binding moiety-L-E where "binding moiety" is a protein interacting binding moiety; L is a conjugation or linking moiety (e.g., a bond or a linking group); and E is an effector moiety. These elements are discussed in the context of additional illustrative examples below. However, while features of each element may be discussed separately, design and selection of an SDC-TRAP can involve the interplay and/or cumulative effect of features of each element (e.g., diffusion, binding, and effect).

Once SDC-TRAP molecules of the invention enter a target cell the effector molecule is released from the SDC-TRAP. In one embodiment, the effector molecule has no activity until it is released from the SDC-TRAP. Accordingly, once the SDC-TRAP molecules enter a target cell an equilibrium exists between free and bound SDC-TRAP molecules. In one embodiment, the effector moiety is only released from the SDC-TRAP when the SDC-TRAP is not associated with the target protein. For example, when an SDC-TRAP molecule is not bound intracellular enzymes can access the linker region thereby freeing the effector moiety. Alternatively, when free SDC-TRAP molecules may be able to release effector molecules through, for example, hydrolysis of the bond or linker that connects the binding moiety and effector moiety.

Accordingly, the rate of effector molecule release and the amount of effector molecule released can be controlled by using binding moieties that bind to the target protein with different affinities. For example, binding moieties that bind to the target protein with lower affinity will be free, resulting in higher concentrations of unbound intracellular SDC-TRAP, and thereby resulting in higher concentrations of free effector molecule. Therefore, in at least one embodiment, irreversibly-binding binding moieties are incompatible with certain aspects of the invention, e.g., those embodiments where effector molecule release is based on free intracellular SDC-TRAP molecules.

In one embodiment, SDC-TRAPs have favorable safety profiles, for example, when compared to, for example, the binding moiety or effector molecule alone. One reason for the increased safety profile is the rapid clearance of SDC-TRAP molecules that do not enter into a target cell.

A number of exemplary SDC-TRAP molecules are set forth in the examples. Specifically a number of Hsp90-specific SDC-TRAP molecules are described and used to demonstrate the efficacy of SDC-TRAP molecules.

Binding Moieties

A primary role of a binding moiety is to ensure that the SDC-TRAP delivers its payload—the effector moiety—to its target by binding to a molecular target in or on a target cell or tissue. In this respect, it is not necessary that the binding moiety also have an effect on the target (e.g., in the case of an Hsp90-targeting moiety, to inhibit Hsp90 in the manner that Hsp90 is are known to do, that is, exhibit pharmacological activity or interfere with its function), but in some embodiments, the binding moiety does have an effect on the target. Accordingly, in various embodiments, an activity of the SDC-TRAP is due solely to the effector moiety exerting a pharmacological effect on the target cell(s), which has been better facilitated by the pharmaceutical conjugate targeting the target cell(s). In other embodiments, an activity of the SDC-TRAP is due in part to the binding moiety—that is, the binding moiety can have an effect beyond targeting.

The molecular target of a binding moiety may or may not be part of a complex or structure of a plurality of biological molecules, e.g., lipids, where the complexes or structures may include lipoproteins, lipid bilayers, and the like. However, in many embodiments, the molecular target to which the binding moiety binds will be free (e.g., cytoplasmic globular protein and/or not be part of a macromolecular assembly or aggregation). The present invention can exploit the selectively high presence of a molecular target in locations of high physiological activity (e.g., Hsp90 in oncological processes). For example, where a drug target is an intracellular drug target, a corresponding molecular target (e.g., Hsp90) can be present in the cell. Likewise, where a drug target is an extracellular drug target, a corresponding molecular target (e.g., Hsp90) can be extracellular, proximal, or associated with the extracellular cell membrane of the target cell or tissue.

In various embodiments, a binding moiety can effect a target cell or tissue (e.g., in the case of an Hsp90-targeting moiety that in fact inhibits Hsp90, for example, Hsp90i). In such embodiments, a pharmacological activity of the binding moiety contributes to, complements, or augments, the pharmacological activity of the effector moiety. Such embodiments go beyond the advantages combination therapies (e.g., a cancer combination therapy of Hsp90i and a second drug such as ganetespib or crizotinib) by providing a therapy that can be carried out by administration of a single SDC-TRAP that realizes both the benefits of the combination therapy and targeting. Other examples of such SDC-TRAPs include conjugates of an Hsp90i (such as ganetespib) and a second cancer drug such as docetaxel or paclitaxel (e.g., in NSCLC); BEZ235 (e.g., in melanoma, prostate and/or NSCLC); temsirolimus (e.g., renal cell carcinoma (RCC), colon, breast and/or NSCLC); PLX4032 (e.g., in melanoma); cisplatin (e.g., colon, breast cancer); AZD8055 (e.g., in NSCLC); and crizotinib (e.g., ALK+ NSCLC).

A range of pharmaceutical activities can be achieved by judicious selection of a binding moiety and an effector moiety. For example, for treating solid tumors, e.g., colon cancer, high continuous doses of antimetabolites such as capecitabine or gemcitabine tend to be required in combination with other drugs. A conjugate having an Hsp90-targeting moiety with lower binding affinity or inhibitory activity to Hsp90, e.g., as determined by a HER2 degradation assay, can be designed to meet this need. Such a conjugate can comprise an effector moiety that is a strong, potent antimetabolite such as 5-FU, to afford a high dose of the conjugate that may be dosed relatively frequently. Such an approach not only achieves the aim of providing a high dose of an antimetabolite fragment at the tumor, but also lowers the toxicity of administering the drug on its own, owing to the plasma stability of SDC-TRAPs of the invention, and the ability of the Hsp90-targeting moiety to deliver the antimetabolite to the desired cells or tissues.

In embodiments where solid tumors such as SCLC or colorectal cancer are to be treated with drugs such as topotecan or irinotecan, only low doses of the drug may be dosed. Due to the very high intrinsic activity of these drugs, an SDC-TRAP should be designed to provide a low dose of such drugs at the target tissue. In this scenario, for example, an Hsp90-targeting moiety having a higher binding affinity or inhibitory activity to Hsp90 (e.g., as determined by a HER2 degradation assay) can sufficiently maintain the presence of the drug in the tissue at a very high level, to ensure that enough of the drug reaches and is retained by the desired target tissue due to the low dosing.

In various illustrative embodiments where a molecular target of a binding moiety is Hsp90, the binding moiety can be an Hsp90-targeting moiety, for example a triazole/resorcinol-based compound that binds Hsp90, or a resorcinol amide-based compound that binds Hsp90, e.g., ganetespib or a tautomer/derivative/analog thereof, AUY-922 or a tautomer/derivative/analog thereof, or AT-13387 or a tautomer/derivative/analog thereof.

In another embodiment, the binding moiety may advantageously be an Hsp90-binding compound of formula (I):

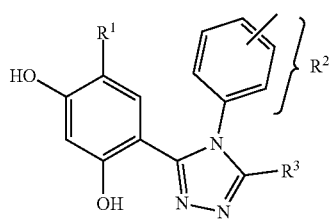

wherein $R^1$ may be alkyl, aryl, halide, carboxamide or sulfonamide; $R^2$ may be alkyl, cycloalkyl, aryl or heteroaryl, wherein when $R^2$ is a 6 membered aryl or heteroaryl, $R^2$ is substituted at the 3- and 4-positions relative to the connection point on the triazole ring, through which a linker L is attached; and $R^3$ may be SH, OH, —CONHR$^4$, aryl or heteroaryl, wherein when $R^3$ is a 6 membered aryl or heteroaryl, $R^3$ is substituted at the 3 or 4 position.

In another embodiment, the binding moiety may advantageously be an Hsp90-binding compound of formula (II):

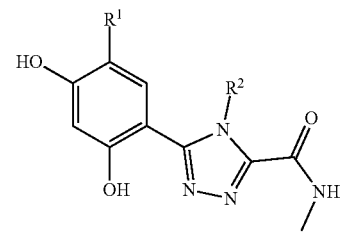

wherein $R^1$ may be alkyl, aryl, halo, carboxamido, sulfonamido; and $R^2$ may be optionally substituted alkyl, cycloalkyl, aryl or heteroaryl. Examples of such compounds include 5-(2,4-dihydroxy-5-isopropylphenyl)-N-(2-morpholinoethyl)-4-(4-(morpholinomethyl)phenyl)-4H-1,2,4-triazole-3-carboxamide and 5-(2,4-dihydroxy-5-isopropylphenyl)-4-(4-(4-methylpiperazin-1-yl)phenyl)-N-(2,2,2-trifluoroethyl)-4H-1,2,4-triazole-3-carboxamide.

In another embodiment, the binding moiety may advantageously be an Hsp90-binding compound of formula (III):

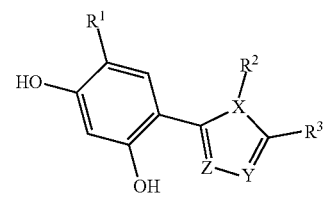

wherein X, Y, and Z may independently be CH, N, O or S (with appropriate substitutions and satisfying the valency of the corresponding atoms and aromaticity of the ring); $R^1$ may be alkyl, aryl, halide, carboxamido or sulfonamido; $R^2$ may be substituted alkyl, cycloalkyl, aryl or heteroaryl, where a linker L is connected directly or to the extended substitutions on these rings; $R^3$ may be SH, OH, NR$^4$R$^5$ AND —CONHR$^6$, to which an effector moiety may be connected; $R^4$ and $R^5$ may independently be H, alkyl, aryl, or heteroaryl; and $R^6$ may be alkyl, aryl, or heteroaryl, having a minimum of one functional group to which an effector moiety may be connected. Examples of such compounds include AUY-922:

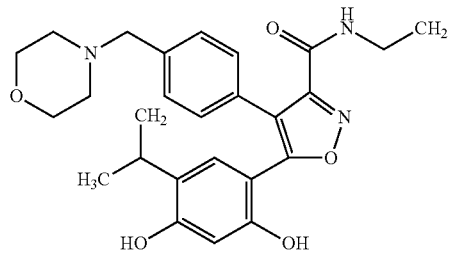 [SMILES: CCNC(=O)c1noc(-c2cc(C(C)C)c(O)cc2O)c1-c1ccc(CN2CCOCC2)cc1]

In another embodiment, the binding moiety may advantageously be an Hsp90-binding compound of formula (IV):

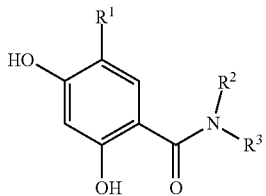

wherein R¹ may be alkyl, aryl, halo, carboxamido or sulfonamido; R² and R³ are independently $C_1$-$C_5$ hydrocarbyl groups optionally substituted with one or more of hydroxy, halogen, $C_1$-$C_2$ alkoxy, amino, mono- and di-$C_1$-$C_2$ alkylamino; 5- to 12-membered aryl or heteroaryl groups; or, R² and R³, taken together with the nitrogen atom to which they are attached, form a 4- to 8-membered monocyclic heterocyclic group, of which up to 5 ring members are selected from O, N and S. Examples of such compounds include AT-13387:

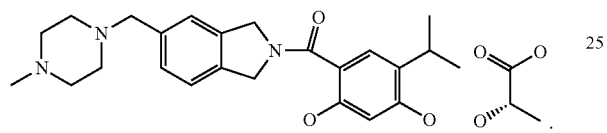

In certain embodiments, to enhance the bioavailability or delivery of the pharmaceutical conjugate, the binding moiety may be a prodrug of the Hsp90-binding compound.

Specific examples of suitable Hsp90-targeting moieties include geldanamycins, e.g.,

IPI-493

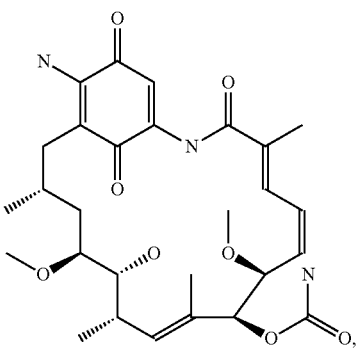

macbecins, tripterins, tanespimycins, e.g.,

17-AAG

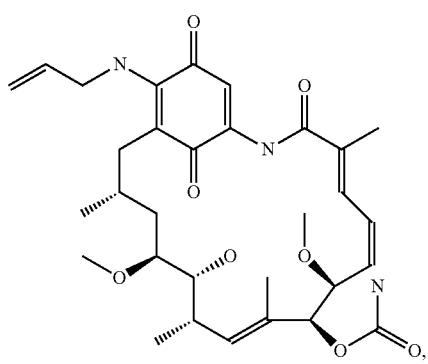

KF-55823

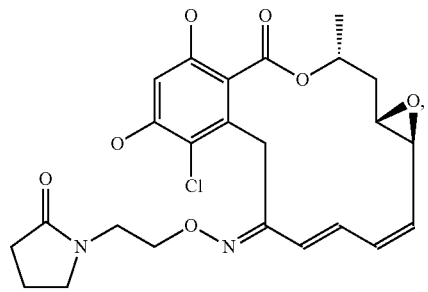

radicicols, KF-58333

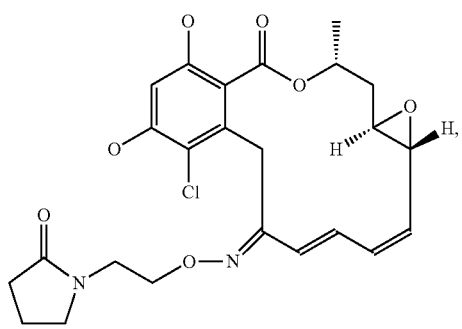

KF-58332

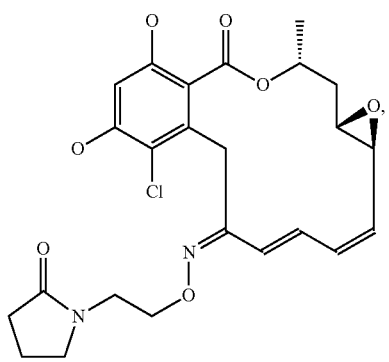

17-DMAG

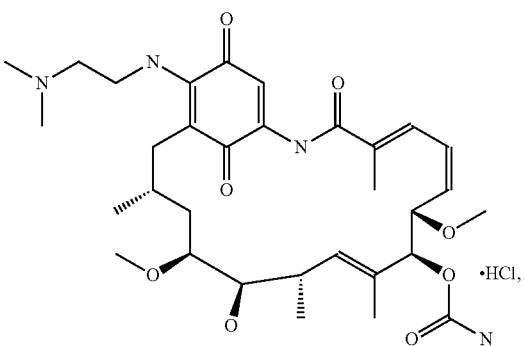

IPI-504
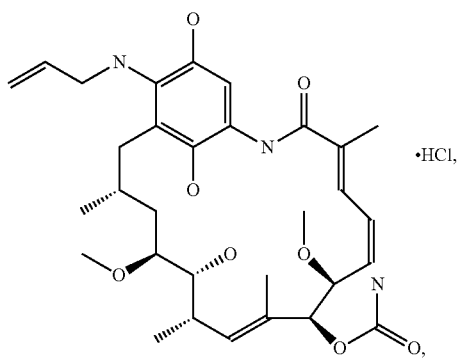
·HCl,
BIIB-021
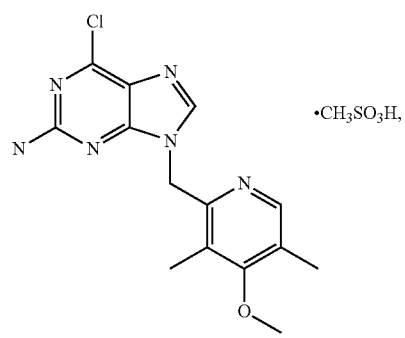
·CH₃SO₃H,
BIIB-028, PU-H64
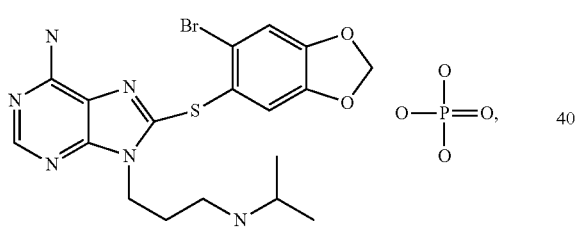
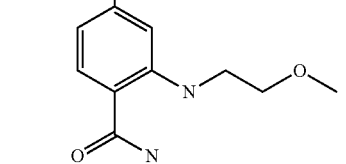,
PU-H71
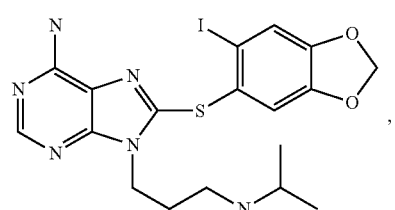,
PU-DZ8
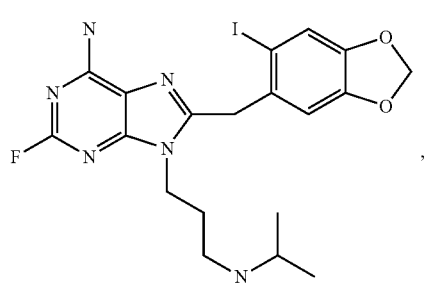,
PU-HZ151
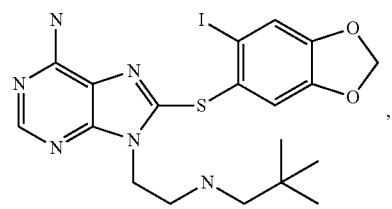,
SNX-2112
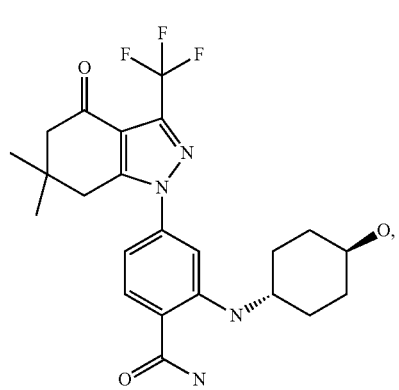,
SNX-2321
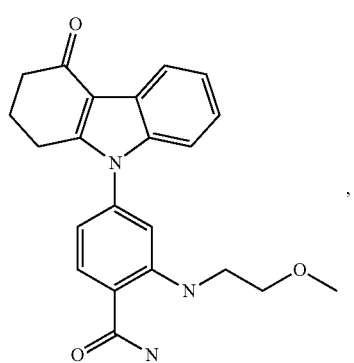,
SNX-5422
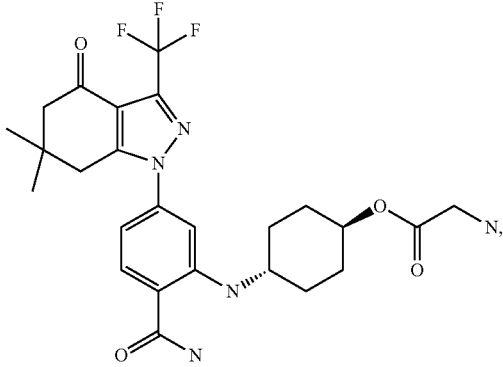, SNX-7081
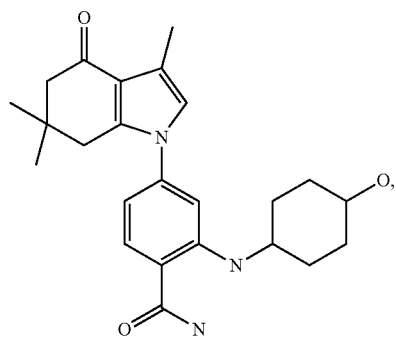
SNX-8891, SNX-0723
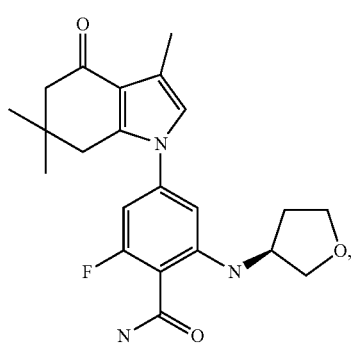
SAR-567530, ABI-287, ABI-328, AT-13387
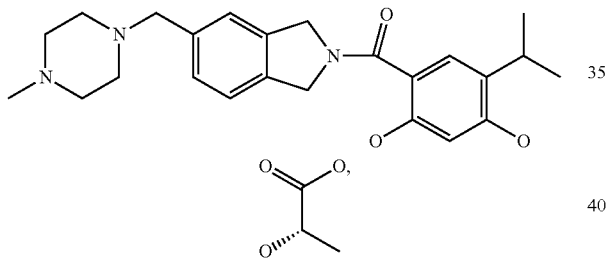
NSC-113497
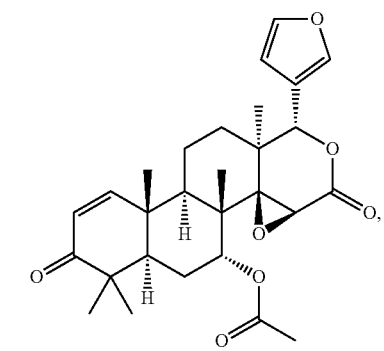
PF-3823863
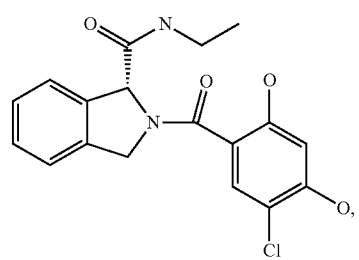
PF-4470296
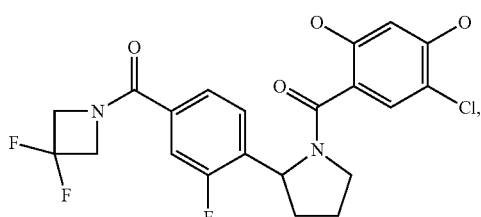
EC-102, EC-154, ARQ-250-RP, BC-274
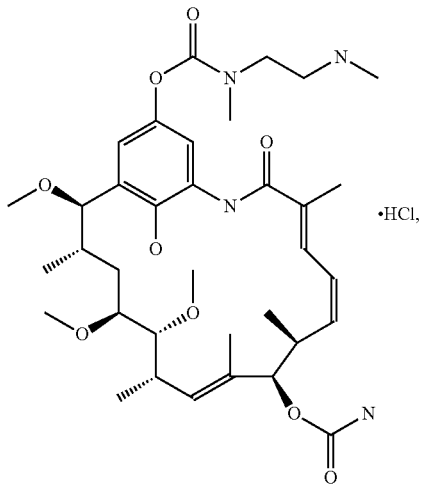
VER-50589
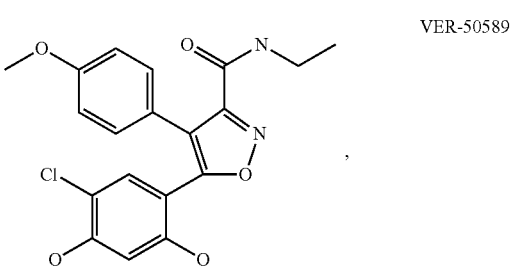
KW-2478
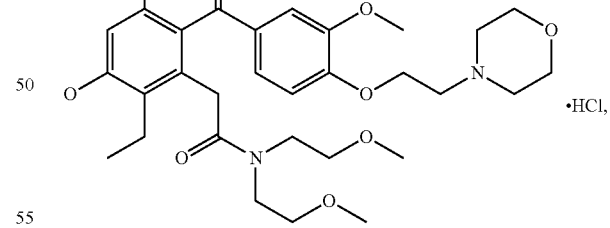
BHI-001, AUY-922
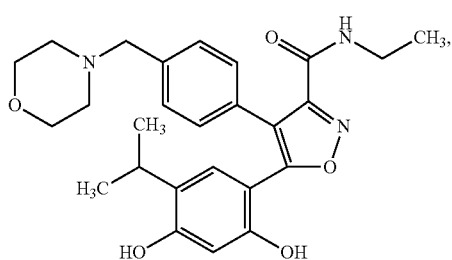

EMD-614684
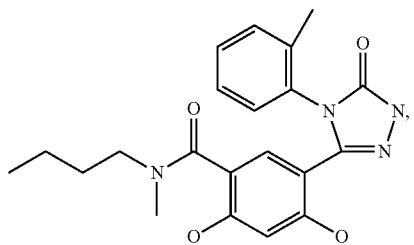
EMD-683671, XL-888, VER-51047
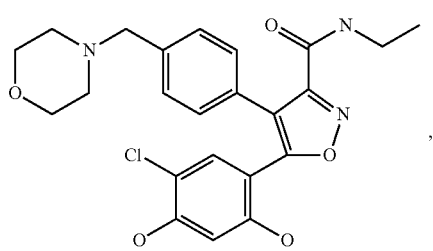
KOS-2484, KOS-2539, CUDC-305
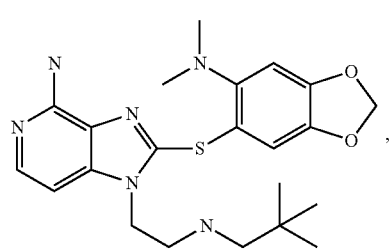
MPC-3100
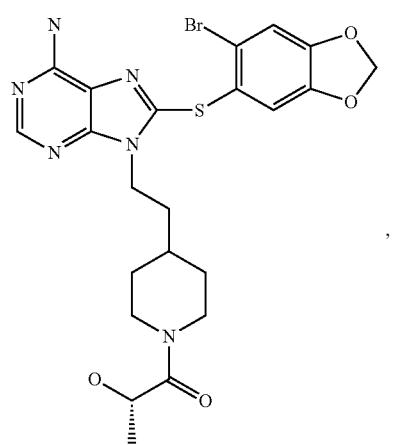
CH-5164840
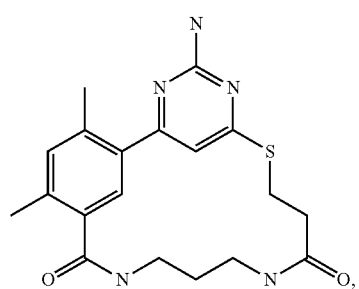
PU-DZ13
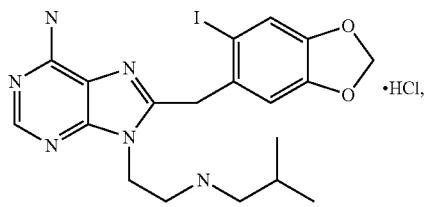
PU-HZ151
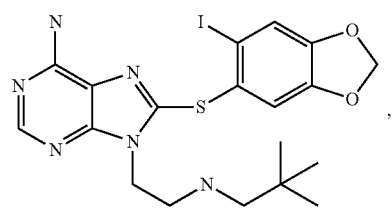
PU-DZ13
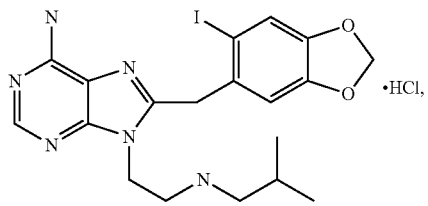
VER-82576
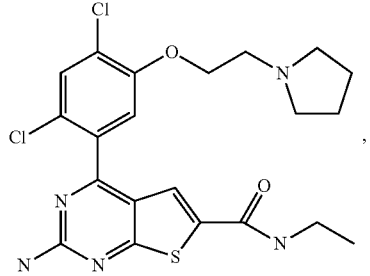
VER-82160
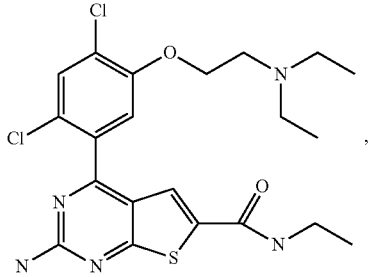
VER-82576
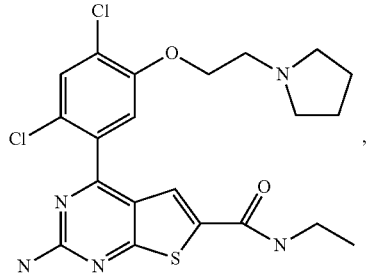

VER-82160

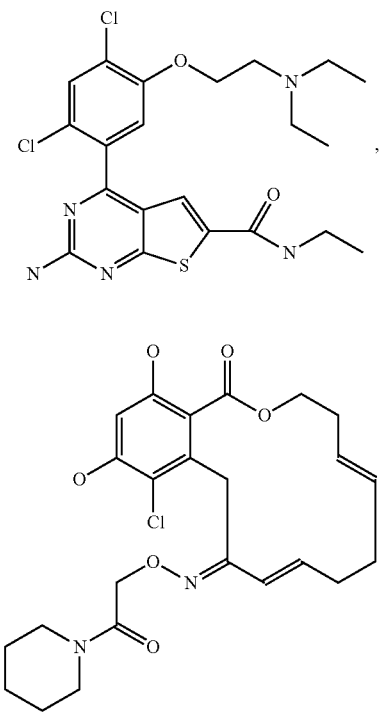

NXD-30001

NVP-HSP990

SST-0201CL1

·HCl,

SST-0115AA1

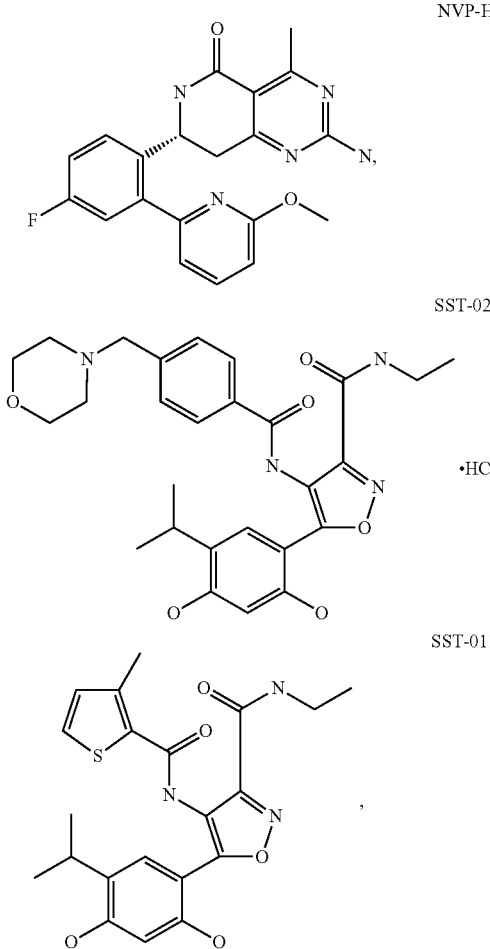

SST-002AA1

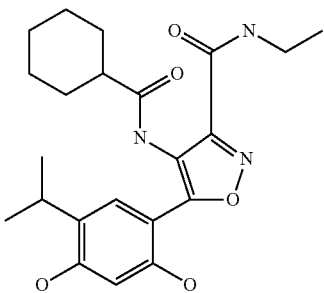

SST-0223AA1

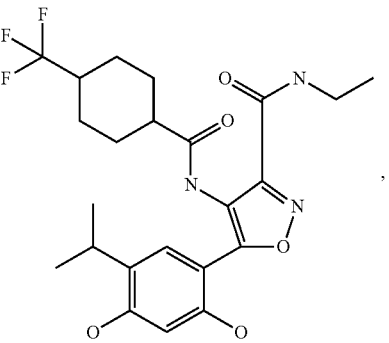

novobiocin (a C-terminal Hsp90i), or a tautomer/derivative/ analog thereof. The selection of other Hsp90-targeting moieties will be within the grasp of one of ordinary skill in the art. Likewise, the selection of binding moieties suitable for other molecular targets and/or other applications will be within the ability of one of ordinary skill in the art.

Additionally Hsp90 targeting moieties can be used to construct SDC-TRAP molecules for the treatment of inflammation. For example, binding moieties comprising the compounds shown in Tables 5, 6, and 7 of U.S. Patent Publication 2010/0280032, which is incorporated herein by reference in its entirety, or compounds of any formula therein, or tautomers, pharmaceutically acceptable salts, solvates, clathrates, hydrates, polymorphs or prodrugs thereof, inhibit the activity of Hsp90 and, thereby cause the degradation of Hsp90 client proteins. Any of these compounds may be coupled to an effector molecule to form an SDC-TRAP. The glucocorticoid receptor is a client protein of Hsp90 and binds to Hsp90 when it is in the conformation that is able to bind glucocorticoid ligands such as cortisol. Once a glucocorticoid binds to GR, the receptor disassociates with Hsp90 and translocates to the nucleus where it modulates gene expression to reduce inflammatory responses such as proinflammatory cytokine production. Thus, glucocorticoids may be given to patients in need of immunosuppression and patients with inflammatory and autoimmune disorders. Unfortunately, although glucocorticoids are effective at relieving inflammation, they have a number of severe side effects including osteoporosis, muscle wasting, hypertension, insulin resistance, truncal obesity and fat redistribution, and inhibition of wound repair. Inhibition of Hsp90 causes changes in GR activity which results in reduction of inflammatory responses similar to those seen for glucocorticoids. However, since the mechanism for reducing inflammation is different than that of glucocorticoids, it is expected that some or all of the side effects of glucocorticoid treatment will be reduced or eliminated.

Effector Moieties

An effector moiety can be any therapeutic or imaging agent that can be conjugated to a binding moiety and, in a thus conjugated state, delivered to a molecular target of the binding moiety. An effector molecule can, in some cases, require a linking moiety for conjugation (e.g., cannot be directly conjugated to a binding moiety). Similarly, an effector molecule can, in some cases, impede or reduce the ability of the binding moiety and/or SDC-TRAP to reach a target as long as the SDC-TRAP can still effect the target. However, in preferred embodiments, an effector moiety is readily conjugatable and may benefits delivery to, and effecting, of the target.

In various embodiments, an SDC-TRAP, via an effector moiety, can have other ways of cell penetration than simple passive diffusion. Such an example is an SDC-TRAP including an antifolate or fragments thereof (e.g., temozolamide, mitozolamide, nitrogen mustards, estramustine, or chloromethine) as the effector moiety. In this case, a conjugate of a binding moiety (e.g., Hsp90 inhibitor) with pemetrexed (or its folate-recognizing fragment) can undergo folate receptor mediated endocytosis rather than passive diffusion. Once in a target cell, the SDC-TRAP can bind the molecular target (e.g., Hsp90 protein) via its binding moiety (e.g., Hsp90 inhibitor).

As described in greater detail below, an effector moiety can comprise a region that can be modified and/or participate in covalent linkage to a binding moiety without substantially adversely affecting the binding moiety's ability to bind to its target. An effector moiety can be a pharmaceutical molecule or a derivative thereof, which essentially retains activity while conjugated to a binding moiety. It will be appreciated that drugs with otherwise good and desirable activity can prove challenging to administer conventionally (e.g., due to poor bioavailability or undesirable side-effects in vivo prior to reaching their target)—such drugs can be "reclaimed" for use as effector moieties in the SDC-TRAPs of the present invention.

Examples of effector moieties include: peptidyl-prolyl isomerase ligands, e.g., FK506; rapamycin, cyclosporin A and the like; steroid hormone receptor ligands, e.g., naturally occurring steroid hormones, such as estrogen, progestin, testosterone, and the like, as well as synthetic derivatives and mimetics thereof; binding moieties that bind to cytoskeletal proteins, e.g., antimitotic agents, such as taxanes, colchicine, colcemid, nocadozole, vinblastine, and vincristine, actin binding agents, such as cytochalasin, latrunculin, phalloidin, and the like; lenalidomide, pomalidomide, camptothecins including

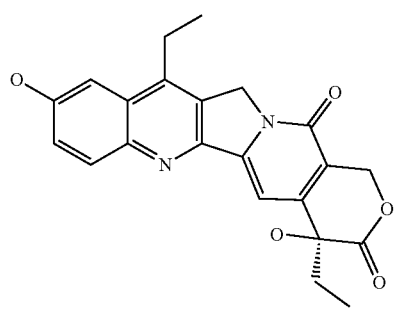

SN-38 topotecan, combretastatins, capecitabine, gemcitabine, vinca alkaloids, platinum-containing compounds, metformin, HDAC inhibitors (e.g., suberoylanilidehydroxamic acid (SAHA)), thymidylate synthase inhibitors such as methotrexate, pemetrexed, and raltitrexed; nitrogen mustards such as bendamustine and melphalan; 5-fluorouracil (5-FU) and its derivatives; and agents used in ADC drugs, such as vedotin and DM1, or a tautomer/derivative/analog thereof.

The effector moiety may be obtained from a library of naturally occurring or synthetic molecules, including a library of compounds produced through combinatorial means, i.e., a compound diversity combinatorial library. When obtained from such libraries, the effector moiety employed will have demonstrated some desirable activity in an appropriate screening assay for the activity. It is contemplated that in other embodiments, the pharmaceutical conjugate may include more than one effector moiety(ies), providing the medicinal chemist with more flexibility. The number of effector moieties linked to the binding moiety (e.g., Hsp90-targeting moiety) will generally only be limited by the number of sites on the binding moiety (e.g., Hsp90-targeting moiety) and/or any linking moiety available for linking to an effector moiety; the steric considerations, e.g., the number of effector moieties than can actually be linked to the binding moiety (e.g., Hsp90-targeting moiety); and that the ability of the pharmaceutical conjugate to bind to the molecular target (e.g., Hsp90 protein) is preserved.

Specific drugs from which the effector moiety may be derived include: psychopharmacological agents, such as central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.); central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics; psychopharmacological/psychotropics, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.); respiratory tract drugs, e.g., central antitussives (opium alkaloids and their derivatives); immunosuppressive agents; pharmacodynamic agents, such as peripheral nervous system drugs, e.g., local anesthetics (ester derivatives, amide derivatives); drugs acting at synaptic or neuroeffector junctional sites, e.g., cholinergic agents, cholinergic blocking agents, neuromuscular blocking agents, adrenergic agents, antiadrenergic agents; smooth muscle active drugs, e.g., spasmolytics (anticholinergics, musculotropic spasmolytics), vasodilators, smooth muscle stimulants; histamines and antihistamines, e.g., histamine and derivative thereof (betazole), antihistamines ($H_1$-antagonists, $H_2$-antagonists), histamine metabolism drugs; cardiovascular drugs, e.g., cardiotonics (plant extracts, butenolides, pentadienolids, alkaloids from erythrophleum species, ionophores, adrenoceptor stimulants, etc.), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics; chemotherapeutic agents, such as anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like; anti-inflammatory agents; antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; β-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones; antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole; anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.; antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate; and antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Conjugation and Linking Moieties

Binding moieties and effector moieties of the present invention can be conjugated, for example, through a linker or linking moiety L, where L may be either a bond or a linking group. For example, in various embodiments, a binding moiety and an effector moiety are bound directly or are parts of a single molecule. Alternatively, a linking moiety can provide a covalent attachment between a binding moiety and effector moiety. A linking moiety, as with a direct bond, can achieve a desired structural relationship between a binding moiety and effector moiety and or an SDC-TRAP and its molecular target. A linking moiety can be inert, for example, with respect to the targeting of a binding moiety and biological activity of an effector moiety.

Appropriate linking moieties can be identified using the affinity, specificity, and/or selectivity assays described herein. Linking moieties can be selected based on size, for example, to provide an SDC-TRAP with size characteristics as described above. In various embodiments, a linking moiety can be selected, or derived from, known chemical linkers. Linking moieties can comprise a spacer group terminated at either end with a reactive functionality capable of covalently bonding to the drug or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linking moieties that may find use in the SDC-TRAPs include disulfides and stable thioether moieties.

In various embodiments, a linking moiety is cleavable, for example enzymatically cleavable. A cleavable linker can be used to release an effector moiety inside a target cell after the SDC-TRAP is internalized. The susceptibility of a linking moiety to cleavage can be used to control delivery of an effector molecule. For example, a linking moiety can be selected to provide extended or prolonged release of an effector moiety in a target cell over time (e.g., a carbamate linking moiety may be subject to enzymatic cleavage by a carboxylesterase via the same cellular process used to cleave other carbamate prodrugs like capecitabine or irinotecan). In these, and various other embodiments, a linking moiety can exhibit sufficient stability to ensure good target specificity and low systemic toxicity, but not so much stability that it results in lowering the potency and efficacy of the SDC-TRAP.

Exemplary linkers are described in U.S. Pat. No. 6,214,345 (Bristol-Myers Squibb), U.S. Pat. Appl. 2003/0096743 and U.S. Pat. Appl. 2003/0130189 (both to Seattle Genetics), de Groot et al., J. Med. Chem. 42, 5277 (1999); de Groot et al. J. Org. Chem. 43, 3093 (2000); de Groot et al., J. Med. Chem. 66, 8815, (2001); WO 02/083180 (Syntarga); Carl et al., J. Med. Chem. Lett. 24, 479, (1981); Dubowchik et al., Bioorg & Med. Chem. Lett. 8, 3347 (1998) and Doronina et al. BioConjug Chem. 2006; Doronina et al. Nat Biotech 2003.

In one embodiment, the SDC-TRAP comprises ganetespib or its tautomer or analog as a binding moiety, and SN-38 or its fragment/derivative/analog as an effector moiety. One non-limiting example is SDC-TRAP-0063. The term SDC-TRAP-0063 includes a compound having a structure of:

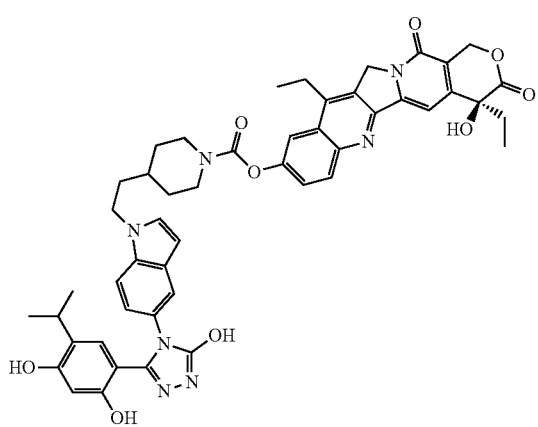 [SMILES: CCc1c2c(nc3ccc(OC(=O)N4CCC(CCn5ccc6cc(-n7c(O)nnc7-c7cc(C(C)C)c(O)cc7O)ccc65)CC4)cc13)-c1cc3c(c(=O)n1C2)COC(=O)[C@]3(O)CC]

or its tautomer:

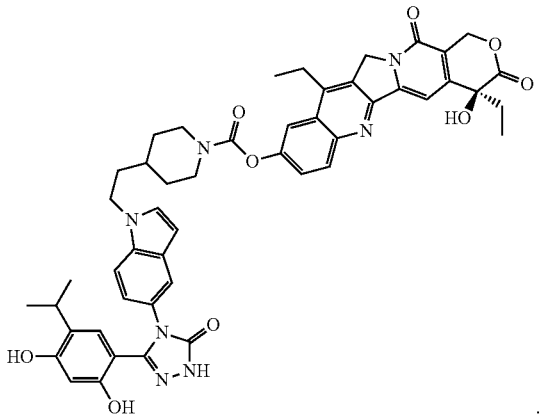 [SMILES: CCc1c2c(nc3ccc(OC(=O)N4CCC(CCn5ccc6cc(-n7c(-c8cc(C(C)C)c(O)cc8O)n[nH]c7=O)ccc65)CC4)cc13)-c1cc3c(c(=O)n1C2)COC(=O)[C@]3(O)CC]

Identification and Selection of Targets and Corresponding SDC-TRAPs

The present invention provides for a broad class of pharmacological compounds including an effector moiety conjugated to a binding moiety directing the effector moiety to a biological target of interest. While treating cancer using an Hsp90 inhibitor binding moiety conjugated to a cytotoxic agent effector moiety is one illustrative example of the present invention, SDC-TRAPs are fundamentally broader in terms of their compositions and uses.

In various embodiments, the broad class of SDC-TRAP pharmacological compounds that are directed to biological targets have the following properties:

the biological target (a cell and/or tissue target of interest, e.g., a tumor) should be effectible by an effector moiety, and the effector moiety should be known or developed for the biological target (e.g., chemotherapeutic agent for the tumor); the biological target should be associated with a molecular target (e.g., biomolecule, capable of being specifically bound, that is uniquely represented in the biological target) that specifically interacts with a binding moiety, and the binding moiety should be known or developed for the molecular target (e.g., ligand for the biomolecule); and the effector moiety and binding moiety should be amenable to coupling and should essentially retain their respective activity after coupling. Furthermore, the conjugate should be capable of reaching and interacting with the molecular target, and in clinical applications should be suitable for administration to a subject (e.g., a subject can tolerate a therapeutically effective dose).

Examples of therapeutic molecular targets (i.e., binding moiety binding partners) for various conditions/disease states are presented in the table below. A suitable binding moiety can be selected based upon a given molecular target and/or a suitable effector moiety can be selected based upon a given condition/disease. In some cases, an FDA approved therapeutic agent can be used as an effector moiety (i.e., where the FDA approved therapeutic agent is an effector moiety as described herein, for example, a binding moiety and not an antibody).

| Condition/Disease State | Molecular target(s) | FDA Approved Therapeutic Agent |
|---|---|---|
| Acute allograft rejection (renal transplant) | CD3E | Muromonab |
| Acromegaly | somatostatin receptor 1 | Octreotide |
| Actinic Keratosis | toll-like receptor 7 | Imiquimod |
| Acute Coronary Syndrome | P2Y12 ADP-receptor | Brilinta |
| Acute Myocardial Infarction | plasminogen | Reteplase |
| alpha$_1$-proteinase inhibitor (A$_1$-PI) deficiency | elastase, neutrophil expressed | Alpha-1 proteinase inhibitor |
| Alzheimer's Disease | BACE1 | |
| Alzheimer's Disease | soluble APP α and APP β | |
| Anemia | erythropoietin receptor | Epoetin alfa |
| Angina, chronic stable | calcium channel, voltage-dependent, L type, alpha 1C subunit | Nicardipine |
| Angina, unstable | P2Y12 ADP-receptor | Brilinta |
| Angioedema, hereditary | kallikrein 1 | Ecallantide |
| Angioedema, acute hereditary | bradykinin B2 receptor | Firazyr |
| Ankylosing spondylitis | tumor necrosis factor | Infliximab |
| Anticoagulant | serpin peptidase inhibitor, clade D (heparin cofactor), member 1 | Ardeparin (withdrawn) |
| Arrhythmia (ventricular) | potassium voltage-gated channel, subfamily H (eag-related), member 2 | Propafenone |
| Arrhythmia | calcium channel, voltage-dependent, P/Q type, alpha 1A subunit | Bepridil |
| Arthritis / rheumatic disorders | dihydroorotate dehydrogenase (quinone) | Leflunomide |
| Arthritis / rheumatic disorders | interleukin 1 receptor, type I | Anakinra |
| Asthma | cysteinyl leukotriene receptor 1 | Nedocromil |
| Asthma | IgE antibodies | Omalizumab |
| Atypical hemolytic uremic syndrome (aHUS) | complement component 5 | Eculizumab |
| Baldness | steroid-5-alpha-reductase, alpha polypeptide 1 (3-oxo-5 alpha-steroid delta 4-dehydrogenase alpha 1) | Finasteride |
| Benign prostatic hyperplasia | steroid-5-alpha-reductase, alpha polypeptide 1 (3-oxo-5 alpha-steroid delta 4-dehydrogenase alpha 1) | Finasteride |
| Bone/vertebral fracture prevention | TGF-beta activated kinase 1/MAP3K7 binding protein 2 | — |
| Breast Cancer | ER (estrogen receptor) | |
| Breast Cancer | HER-2/neu | Trastuzumab (HER-2) |
| Breast Cancer | tubulin, beta 1 class VI | Paclitaxel |
| Breast Cancer | chromodomain helicase DNA binding protein 1 | Epirubicin |
| Breast Cancer | Tubulin | Halaven |
| Breast/Ovarian Cancer | BRCA genes | |
| Bronchitis, chronic | phosphodiesterase 4 (PDE4) inhibitors | Daliresp |
| Cardiac Ischemic Conditions | integrin, beta 3 (platelet glycoprotein IIIa, antigen CD61) | Abciximab |
| Cancer | CD74; Trop-2; CEACAM6 | |
| Cancer | EGFR | |
| Cardiovascular disease | Matrix Mettaloproteinases | |
| Cardiovascular disease | VKORC1 | |
| Cardiovascular disease | LDL | |
| Cervical Dystonia | vesicle-associated membrane protein 1 (synaptobrevin 1) | Botulinum toxin type B |
| Chemoprotectant | alkaline phosphatase, placental-like 2 | Amifostine |
| Chronic myelogenous leukemia | interferon (alpha, beta and omega) receptor 1 | Interferon alfa-2a |
| Chronic Obstmctive Pulmonary Disorder | phosphodiesterase 4 (PDE4) inhibitors | Daliresp |
| Chronic spasticity due to upper motor disorders | ryanodine receptor 1 (skeletal) | Dantrolene |
| Colon Cancer | guanylate cyclase 2C | |
| Colorectal Cancer | EGFR | |
| Colorectal Cancer | KRAS | |
| Colorectal Cancer | CEA | |
| Congestive Heart Failure | B-type natriuretic peptide | |
| Congestive Heart Failure | plasminogen | Reteplase |
| Crohn's Disease | integrin, alpha 4 (antigen CD49D, alpha 4 subunit of VLA-4 receptor) | Natalizumab |
| Cryopyrin-associated periodic syndromes | interleukin 1, beta | Canakinumab |
| Cryopyrin-associated periodic syndromes | interleukin 1, alpha | Rilonacept |
| Depression | 5HT1A receptor (a serotonin reuptake inhibitor) | Viibryd |
| Diabetes | dipeptidyl peptidase-4 (DPP-4) enzyme | Tradjenta |
| Diabetes | protein kinase, AMP-activated, beta 1 non-catalytic subunit | Metformin |

-continued

| Condition/Disease State | Molecular target (s) | FDA Approved Therapeutic Agent |
|---|---|---|
| Diabetes | amylase, alpha 2A (pancreatic) | Acarbose |
| Diabetes | peroxisome proliferator-activated receptor gamma | Troglitazone (withdrawn) |
| Diabetes | glucagon-like peptide 1 receptor | Exenatide |
| Diabetes | receptor (G protein-coupled) activity modifying protein 1 | Pramlintide |
| Diabetes | dipeptidyl-peptidase 4 | Sitagliptin |
| Edema | potassium voltage-gated channel, Isk-related family, member 1 | Indapamide |
| Edema | solute carrier family 12 (sodium/potassium/chloride transporters), member 2 | Bumetanide |
| Factor XIII (FXIII) deficiency, congenital | enzyme replacement therapy (FactorXIII) | Corifact |
| Familial cold autoinflammatofy syndrome | interleukin 1, beta | Canakinumab |
| Familial cold autoinflammatofy syndrome | interleukin 1, alpha | Rilonacept |
| Gaucher Disease, type I | UDP-glucose ceramide glucosyltransferase | Miglustat |
| GI stromal tumors (GIST), metastatic malignant | Bcr-Abl tyrosine kinase (an abnormal tyrosine kinase) | |
| Glaucoma | prostaglandin F receptor (FP) | Latanoprost |
| Granulomatous disease, chronic | interferon gamma receptor 1 | Interferon gamma- lb |
| Growth disorder | insulin-like growth factor 1 receptor | Mecasermin |
| Growth hormone deficiency | growth hormone releasing hormone receptor | Sermorelin |
| Hairy cell leukemia | interferon (alpha, beta and omega) receptor 1 | Interferon alfa-2a |
| Hairy cell leukemia | adenosine deaminase | Pentostatin |
| Heartburn (Gastric reflux) | 5-hydroxytryptamine (serotonin) receptor 4, G protein-coupled | Cisapride (withdrawn) |
| Hemophilia (prevent bleeding) | plasminogen activator, tissue | Tranexamic acid |
| Hepatitis C | interferon (alpha, beta and omega) receptor 1 | Interferon alfa-2a |
| Hepatitis C (genotype 1) | hepatitis C virus non-structural protein 3 (N53) serine protease | Victrelis |
| Hepatitis C (genotype 1) | hepatitis C virus non-structural protein 3 (N53)/4A serine protease | Incivek |
| Hepatocellular Carcinoma | α-fetoprotein | |
| HIV | chemokine (C-C motif) receptor 5 (gene/pseudogene) | Maraviroc |
| HIV | HIV-1 reverse transcriptase | Edurant |
| Hyperammonemia | carbamoyl-phosphate synthase 1, mitochondrial | Carglumic acid |
| Hypercalcemia in patients with parathyroid carcinoma | calcium-sensing receptor | Cinacalcet |
| Hypercholesterolemia | 3-hydroxy-3-methylglutafyl-CoA reductase | Lovastatin |
| Hyperlipidemia | NPC1 (Niemann-Pick disease, type Cl, gene)-like 1 | Ezetimibe |
| Hyperplasia | steroid-5-alpha-reductase, alpha polypeptide 1 (3-oxo-5 alpha-steroid delta 4-dehydrogenase alpha 1) | Finasteride |
| Hypertension | adrenoceptor alpha 1D | Terazosin |
| Hypertension | calcium channel, voltage-dependent, P/Q type, alpha 1A subunit | Bepridil |
| Hypertension | calcium channel, voltage-dependent, N type, alpha 1B subunit | Amlodipine |
| Hypertension | angiotensin II receptor, type | Losartan |
| Hypertension | renin | Aliskiren |
| Hypertension | AT1 subtype angiotensin II receptor | Edarbi |
| Hypertension | membrane metallo-endopeptidase | Candoxatril |
| Increase bone density, prevent bone fracture | parathyroid hormone 1 receptor | Teriparatide |
| Infections, acute skin and skin structure | penicillin-binding proteins | Teflaro |
| Infections, bacterial | dipeptidase 1 (renal) | Cilastatin (adjuvant) |
| Infections (bone marrow transplant, etc.) | colony stimulating factor 3 receptor (granulocyte) | Filgrastim |
| Infections, immunomodulatory agents | colony stimulating factor 2 receptor, alpha, low-affinity (granulocyte-macrophage) | Sargramostim |
| Infertility | follicle stimulating hormone receptor | Urofollitropin |
| Inflammation | C Reactive Protein | |
| Interstitial cystitis, bladder pain/discomfort due to | fibroblast growth factor 1 (acidic) | Pentosan polysulfate |
| Irritable Bowel Syndrome | chloride channel, voltage-sensitive 2 | Lubiprostone |
| Kaposi's sarcoma, AIDS-related | interferon (alpha, beta and omega) receptor 1 | Interferon alfa-2a |
| Leukemia/Lymphoma | CD20 Antigen | |
| Leukemia/Lymphoma | CD30 | |

-continued

| Condition/Disease State | Molecular target (s) | FDA Approved Therapeutic Agent |
|---|---|---|
| Leukemia/Lymphoma | PML/RAR alpha | |
| Leukemia, chronic myeloid | proto-oncogene tyrosine-protein kinase Src | Dasatinib |
| Leukemia, myeloid | CD33, Myeloid cell surface antigen CD33 | Gemtuzumab ozogamicin (withdrawn) |
| Lipodystrophy | human GRF receptors | Egrifta |
| Lung Cancer | ALK | |
| Lung Cancer | CD98; fascin; 14-3-3 eta | |
| Lymphocytic leukemia, B-cell chronic | polymerase (DNA directed), alpha 1, catalytic subunit | Fludarabine |
| Lymphocytic leukemia, B-cell chronic | CD52 (CAMPATH-1 antigen precursor) | Alemtuzumab |
| Lymphocytic leukemia, chronic | membrane-spanning 4-domains, subfamily A, member 1 | Rituximab |
| Lymphoma, Hodgkin's | chemokine (C-X-C motif) receptor 4 | Plerixafor |
| Lymphoma, Hodgkin's | CD30 | Adcetris |
| Lymphoma, mantle cell | proteasome (prosome, macropain) subunit, beta type, 1 | Bortezomib |
| Lymphoma, systemic anaplastic large cell | CD30 | Adcetris |
| Lymphocytic leukemia, T-cell | histone deacetylase 1 | Vorinostat |
| Melanoma | S100 protein | |
| Melanoma, metastatic (with BRAFV600E mutation) | mutated form of BRAf that facilitates cell growth | Zelboraf |
| Melanoma, metastatic | CTLA-4 | Yervoy |
| Migraine Headache | carbonic anhydrase II | Topiramate |
| Muckle-Wells syndrome | interleukin 1, beta | Canakinumab |
| Muckle-Wells syndrome | interleukin 1, alpha | Rilonacept |
| Multiple Sclerosis | sphingosine-1-phosphate receptor 1 | Fingolimod |
| Myeloma, multiple | chemokine (C-X-C motif) receptor 4 | Plerixafor |
| Myeloma, multiple | proteasome (prosome, macropain) subunit, beta type, 1 | Bortezomib |
| Myocardial Infarction | Troponin I | |
| Myocardial Infarction, non-ST-elevation | P2Y12 ADP-receptor | Brilinta |
| Myocardial Infarction, ST-elevation | P2Y12 ADP-receptor | Brilinta |
| N-acetylglutamate synthase (NAGS) deficiency | carbamoyl-phosphate synthase 1, mitochondrial | Carglumic acid |
| Nausea/vomiting | 5-hydroxynyptamine (serotonin) receptor 3A, ionotropic | Ondansetron |
| Nausea/vomiting | tachykinin receptor 1 | Aprepitant |
| Nausea/vomiting (severe) | cannabinoid receptor 1 (brain) | Marinol |
| Non-Hodgkin's Lymphoma | membrane-spanning 4-domains, subfamily A, member 1 | Rituximab |
| Non-small cell lung cancer | phosphoribosylglycinamide formyltransferase, phosphoribosylglycinamide synthetase, phosphoribosylaminoimidazole synthetase | Pemetrexed |
| Non-small cell lung cancer | epidermal growth factor receptor | Gefitinib |
| Non-small cell lung cancer (that is ALK-positive) | the ATP-binding pocket of target protein kinases | Xalkori |
| Obesity | lipase, gastric/pancreatic lipase | Orlistat |
| Ovarian Cancer | IGF-II; leptin; osteopontin; prolactin | |
| Oral mucositis | fibroblast growth factor receptor 2 | Palifermin |
| Organ rejection prophylaxsis | FK506 binding protein 1A, 12kDa | Tacrolimus |
| Organ rejection prophylaxis | IMP (inosine 5'-monophosphate) dehydrogenase 2 | Mycophenolate mofetil |
| Organ rejection prophylaxsis | interleukin 2 receptor, alpha | Daclizumab |
| Organ rejection prophylaxsis | FK506 binding protein 12-rapamycin associated protein 1 | Sirolimus |
| Organ rejection prophylaxsis | protein phosphatase 3, regulatory subunit B, beta | Cyclosporine |
| Organ rejection prophylaxsis | CD80 and CD86, blocks CD28 mediated costimulation of T lymphocytes | Nulojix |
| Osteoporosis | interferon gamma receptor 1 | Interferon gamma-lb |
| Osteoporosis (prophylaxsis) | TGF-beta activated kinase 1/MAP3K7 binding protein 2 | Denosumab |
| Paget's Disease | farnesyl diphosphate synthase | Pamidronate |
| Pancreatic Cancer | CA19-9 | |
| Parkinson's Disease | catechol-O-methyltransferase | Tolcapone (withdrawn) |
| Parkinson's Disease | monoamine oxidase B | Selegiline |
| Paroxysmal nocturnal hemoglobinuria | complement component 5 | Eculizumab |

| Condition/Disease State | Molecular target (s) | FDA Approved Therapeutic Agent |
|---|---|---|
| Pneumonia, susceptible bacterial community-acquired | penicillin-binding proteins | Teflaro |
| Poisoning, ethylene glycol or methanol | alcohol dehydrogenase 1B (class I), beta polypeptide | Fomepizole |
| Psoriasis, plaque | interleukin 12B (natural killer cell stimulatory factor 2, cytotoxic lymphocyte maturation factor 2, p40) | Ustekinumab |
| Psoriasis, plaque | integrin, alpha L (antigen CD11A (p180), lymphocyte function-associated antigen 1; alpha polypeptide) | Efalizumab (withdrawn) |
| Psoriasis, chronic plaque | T-cell surface antigen CD2 precursor | Alefacept |
| Psoriatic Arthritis | tumor necrosis factor | Infliximab |
| Prostate Cancer | PSA (prostate specific antigen) | |
| Prostate hyperplasia, benign | adrenoceptor alpha 1D | Terazosin |
| Pulmonary embolism | Factor Xa | Xarelto |
| Pulmonary hypertension | endothelin receptor type B | Bosentan |
| Renal cell carcinoma | v-raf-1 murine leukemia viral oncogene homolog 1 | Sorafenib |
| Renal cell carcinoma | fms-related tyrosine kinase 1 (vascular endothelial growth factor/vascular permeability factor receptor) | Sunitinib |
| Renal cell carcinoma | vascular endothelial growth factor A | Bevacizumab |
| Rheumatoid arthritis | TNF-α | |
| Rheumatoid arthritis | IL-6 | |
| Rheumatoid arthritis | inhibitor of kappa light polypeptide gene enhancer in B-cells, kinase beta | Auranofin |
| Rheumatoid arthritis | tumor necrosis factor | Infliximab |
| Rheumatoid arthritis | CD80 (T-lymphocyte activation antigen CD80) | Abatacept |
| Rheumatoid arthritis | interleukin 6 receptor | Tocilizumab |
| Rheumatoid arthritis | CEP-1 | |
| Schizophrenia | CYP2D6 | |
| Scorpion stings | venom toxins | Anascorp |
| Seizures | carbonic anhydrase II | Topiramate |
| Seizures | solute carrier family 6 (neurotransmitter transporter, GABA), member 1 | Tiagabine |
| Seizures | 4-aminobutyrate aminotransferase | Divalproex sodium |
| Seizures | Gamma-amino butyric acid (GABA) | |
| Sepsis, severe | coagulation factor VIII (Factors Va and VIIIa), procoagulant component | Drotrecogin alfa |
| Small Cell Lung Cancer | topoisomerase (DNA) II alpha 170kDa | Etoposide |
| Small Cell Lung Cancer | topoisomerase (DNA) I | Topotecan |
| Stroke | thrombin | Pradaxa |
| Stroke | Factor Xa | Xarelto |
| Stroke, thrombotic | purinergic receptor P2Y, G-protein coupled, 12 | Ticlopidine |
| Systemic embolism | Factor Xa | Xarelto |
| systemic embolism in non-valvular atrial fibrillation | thrombin | Pradaxa |
| Systemic lupus erythematosus | human B lymphocyte stimulator protein (BLyS) | Benlysta |
| Testicular Cancer | LDH | |
| Thyroid Cancer Metastasis | Thyro-globulin | |
| Thrombocythemia | phosphodiesterase 4B, cAMP-specific | Amrinone |
| Thrombocytopenia | myeloproliferative leukemia virus oncogene expression product | Romiplostim |
| Thrombocytopenia | interleukin 11 receptor, alpha | Oprelvekin |
| Thrombosis, Deep vein | Factor Xa | Xarelto |
| Thyroid Cancer | protein kinases of the VEGF, EGFR, and/or RET pathways | Caprelsa |
| Tyrosinemia type I, hereditary | 4-hydroxyphenylpyruvate dioxygenase | Nitisinone |
| Ulcer (anti-ulcer agent) | ATPase, H+/K+ exchanging, alpha polypeptide | Omeprazole |
| Ulcers, diabetic neuropathic | platelet-derived growth factor receptor, beta polypeptide | Becaplermin |
| Urothelial Cell Carcinoma | Bladder Tumor Antigen | |

Examples of imaging/diagnostic molecular targets (i.e., binding moiety binding partners) for various conditions/disease states are presented in the table below. A suitable binding moiety can be selected based upon a given molecular target and/or a suitable effector moiety can be selected based upon a given condition/disease. In some cases, an FDA approved imaging/diagnostic agent can be used as an effector moiety (i.e., where the FDA approved imaging/diagnostic agent is an effector moiety as described herein, for example, a binding moiety and not an antibody).

| Condition/Disease State | Molecular target (s) | FDA Approved Imaging/Diagnostic |
|---|---|---|
| Alzheimer's disease, stroke, schizophrenia | cerebral blood flow (hemoglobin) | |
| Alzheimer's disease | β-amyloid protein (can be used to monitor progression of the disease) | |
| Diagnostic (screening test for exocrine pancreatic insufficiency and to monitor the adequacy of supplemental pancreatic therapy) | pancreatic lipase | Bentiromide |
| Diagnostic for bone density | parathyroid hormone 1 receptor | Teriparatide |
| Diagnostic/imaging | proteasome (prosome, macropain) subunit, alpha type, 6 pseudogene 1 | Capromab |
| Diagnostic for MRI to visualize blood brain barrier/abnormal vascularity of the CNS (to diagnose disorders of the brain and spine) | Paramagnetic macrocyclic contrast agent | Gadavist |
| General Cognitive Decline (Dementia, Alzheimer's Disease, Parkinson's Disease, etc.) | thinning of the cerebral cortex | |
| Inflammation/tumor progression | (radiolabeled) 18F-fludeoxyglucose | |
| Osteoarthritis | cartilage (collagen and proteoglycan) degeneration | |
| Parkinson's syndrome | Dopamine receptors (diagnostic that detects dopamine receptors) | DaTscan |
| Thyroid Cancer | thyroid stimulating hormone receptor | Thyrotropin alfa |

Imaging Moieties, and Diagnostic and Research Applications

In various embodiments, the effector moiety is an imaging moiety—that is, a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

Imaging studies can be used, for example, in a clinical or research setting to diagnose a subject, select a subject for therapy, select a subject for participation in a clinical trial, monitor the progression of a disease, monitor the effect of therapy, to determine if a subject should discontinue or continue therapy, to determine if a subject has reached a clinical end point, and to determine recurrence of a disease. Imaging studies can be used, for example, to conduct research to identify effective interacting moieties and/or effector moieties and/or combinations thereof, to identify effective dosing and dose scheduling, to identify effective routes of administration, and to identify suitable targets (e.g., diseases susceptible to particular treatment).

Methods of Making Pharmaceutical Conjugates

The pharmaceutical conjugates, i.e., SDC-TRAPs, of the invention may be prepared using any convenient methodology. In a rational approach, the pharmaceutical conjugates are constructed from their individual components, binding moiety, in some cases a linker, and effector moiety. The components can be covalently bonded to one another through functional groups, as is known in the art, where such functional groups may be present on the components or introduced onto the components using one or more steps, e.g., oxidation reactions, reduction reactions, cleavage reactions and the like. Functional groups that may be used in covalently bonding the components together to produce the pharmaceutical conjugate include: hydroxy, sulfhydryl, amino, and the like. The particular portion of the different components that are modified to provide for covalent linkage will be chosen so as not to substantially adversely interfere with that components desired binding activity, e.g., for the effector moiety, a region that does not affect the target binding activity will be modified, such that a sufficient amount of the desired drug activity is preserved. Where necessary and/or desired, certain moieties on the components may be protected using blocking groups, as is known in the art, see, e.g., Green & Wuts, Protective Groups in Organic Synthesis (John Wiley & Sons) (1991).

Alternatively, the pharmaceutical conjugate can be produced using known combinatorial methods to produce large libraries of potential pharmaceutical conjugates which may then be screened for identification of a bifunctional, molecule with the pharmacokinetic profile. Alternatively, the pharmaceutical conjugate may be produced using medicinal chemistry and known structure-activity relationships for the targeting moiety and the drug. In particular, this approach will provide insight as to where to join the two moieties to the linker.

A number of exemplary methods for preparing SDC-TRAP molecules are set forth in the examples. As one of skill in the art will understand, the exemplary methods set forth in the examples can be modified to make other SDC-TRAP molecules.

Methods of Use, Pharmaceutical Preparations, and Kits

The pharmaceutical conjugates find use in treatment of a host condition, e.g., a disease condition. In these methods, an effective amount of the pharmaceutical conjugate is administered to the host, where "effective amount" means a dosage sufficient to produce the desired result, e.g., an improvement in a disease condition or the symptoms associated therewith. In many embodiments, the amount of drug in the form of the pharmaceutical conjugate that need be administered to the host in order to be an effective amount will vary from that which must be administered in free drug form. The difference in amounts may vary, and in many embodiments, may range from two-fold to ten-fold. In certain embodiments, e.g., where the resultant modulated pharmacokinetic property or properties result(s) in enhanced activity as compared to the free drug control, the amount of drug that is an effective amount is less than the amount of corresponding free drug that needs to be administered, where the amount may be two-fold, usually about four-fold and more usually about ten-fold less than the amount of free drug that is administered.

The pharmaceutical conjugate may be administered to the host using any convenient means capable of producing the desired result. Thus, the pharmaceutical conjugate can be incorporated into a variety of formulations for therapeutic administration. More particularly, the pharmaceutical conjugate of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the pharmaceutical conjugate can be achieved in various ways, including oral, buccal, rectal, parenteral, intraperitoneal, intradermal, transdermal, intracheal, etc., administration. In pharmaceutical dosage forms, the pharmaceutical conjugate may be administered alone or in combination with other pharmaceutically active compounds.

The subject methods find use in the treatment of a variety of different disease conditions. In certain embodiments, of particular interest is the use of the subject methods in disease conditions where an active agent or drug having desired activity has been previously identified, but which active agent or drug does not bind to its target with desired affinity and/or specificity. With such active agents or drugs, the subject methods can be used to enhance the binding affinity and/or specificity of the agent for its target.

The specific disease conditions treatable by with the subject bifunctional compounds are as varied as the types of drug moieties that can be present in the pharmaceutical conjugate. Thus, disease conditions include cellular proliferative diseases, such as neoplastic diseases, autoimmune diseases, central nervous system or neurodegenerative diseases, cardiovascular diseases, hormonal abnormality diseases, infectious diseases, and the like.

By treatment is meant at least an amelioration of the symptoms associated with the disease condition afflicting the host, where amelioration is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

Methods of use of the invention extend beyond strict treatment of a disease. For example, the invention includes uses in a clinical or research setting to diagnose a subject, select a subject for therapy, select a subject for participation in a clinical trial, monitor the progression of a disease, monitor the effect of therapy, to determine if a subject should discontinue or continue therapy, to determine if a subject has reached a clinical end point, and to determine recurrence of a disease. The invention also includes uses in conducting research to identify effective interacting moieties and/or effector moieties and/or combinations thereof, to identify effective dosing and dose scheduling, to identify effective routes of administration, and to identify suitable targets (e.g., diseases susceptible to particular treatment).

A variety of hosts are treatable according to the subject methods. Generally such hosts are "mammals" or "mammalian," where these terms are used broadly to describe organisms which are within the class Mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The invention provides kits for treating a subject in need thereof comprising at least one SDC-TRAP and instruction for administering a therapeutically effective amount of the at least one SDC-TRAP to the subject, thereby treating the subject. The invention also provides kits for imaging, diagnosing, and/or selecting a subject comprising at least one SDC-TRAP and instruction for administering an effective amount of at least one SDC-TRAP to the subject, thereby imaging, diagnosing, and/or selecting the subject.

Kits with unit doses of the pharmaceutical conjugate, usually in oral or injectable doses and often in a storage stable formulation, are provided. In such kits, in addition to the containers containing the unit doses, an informational package insert describing the use and attendant benefits of the drugs in treating pathological condition of interest will be included. Preferred compounds and unit doses are those described herein above.

The invention also provides methods for treatment of a disease or disorder in which the subject to be treated is selected for treatment based on the presence of, or the overexpression of, a particular protein. For example, subjects may be selected for treatment of cancer based on the presence of greater the normal levels of Hsp90. In this case, subjects would be administered an SDC-TRAP that comprises a binding moiety that selectively binds to Hsp90.

The invention provides methods of treating or preventing an inflammatory disorder in a subject, comprising administering to the subject an effective amount of a compound represented by any one of formula (I) through (LXXII), or any embodiment thereof, or a compound shown in Table 5, 6, or 7 as disclosed in U.S. Patent Publication 2010/0280032. In one embodiment, the compound or binding moiety or SDC-TRAP may be administered to a human to treat or prevent an inflammatory disorder. In another embodiment, the inflammatory disorder is selected from the group consisting of transplant rejection, skin graft rejection, arthritis, rheumatoid arthritis, osteoarthritis and bone diseases associated with increased bone resorption; inflammatory bowel disease, ileitis, ulcerative colitis, Barrett's syndrome, Crohn's disease; asthma, adult respiratory distress syndrome, chronic obstructive airway disease; corneal dystrophy, trachoma, onchocerciasis, uveitis, sympathetic ophthalmitis, endophthalmitis; gingivitis, periodontitis; tuberculosis; leprosy; uremic complications, glomerulonephritis, nephrosis; sclerodermatitis, psoriasis, eczema; chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immune-complex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma. In another embodiment, an SDC-TRAP, or a compound shown in Table 5, 6, or 7 as disclosed in U.S. Patent Publication 2010/0280032, is administered with an additional therapeutic agent. In another embodiment, the additional therapeutic agent may an anti-inflammatory agent.

In one embodiment, an SDC-TRAP that is administered to a subject but does not enter a target cell is rapidly cleared from the body. In this embodiment, the SDC-TRAP that does not enter a target cell is rapidly cleared in order to reduce the toxicity due to the components of the SDC-TRAP, the degradation products of the SDC-TRAP or the SDC-TRAP molecule. Clearance rate can be determined by measuring the plasma concentration of the SDC-TRAP molecule as a function of time.

Likewise, SDC-TRAP molecules that enter non-targeted cells by passive diffusion rapidly exit the non-targeted cell or tissue and are either eliminated from the subject or proceed to enter and be retained a targeted cell or tissue. For example, an SDC-TRAP that is intended to treat tumor cells and is targeted to tumor cells that overexpress, for example, Hsp90 will accumulate selectively in tumor cells that overexpress Hsp90. Accordingly, very low levels of this exemplary SDC-TRAP will be present in non-tumor tissue such as normal lung tissue, heart, kidney, and the like. In one embodiment, the safety of the SDC-TRAP molecules of the invention can be determined by their lack of accumulation in non-targeted tissue. Conversely, the safety of the SDC-TRAP molecules of the invention can be determined by their selective accumulation in the targeted cells and/or tissue.

EXAMPLES

The following examples, which are briefly summarized and then discussed in turn below, are offered by way of illustration and not by way of limitation.

Example 1: Manufacture of an Exemplary SDC-TRAP

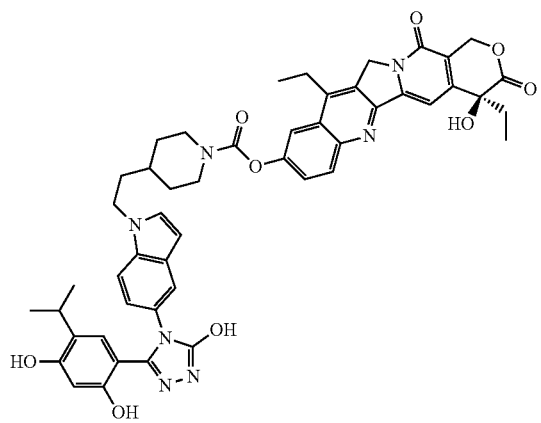

((S)-4,11-diethyl-4-hydroxy-3,14-dioxo-3,4,12,14-tetrahydro-1H-pyrano[3',4':6,7]indolizino[1,2-b]quinolin-9-yl 4-(2-(5-(3-(2,4-dihydroxy-5-isopropylphenyl)-5-hydroxy-4H-1,2,4-triazol-4-yl)-1H-indol-1-yl)ethyl)piperidine-1-carboxylate) or its tautomer.

The manufacture of SDC-TRAP-0063 consisted of three chemical steps and two recrystallization steps, as shown below.

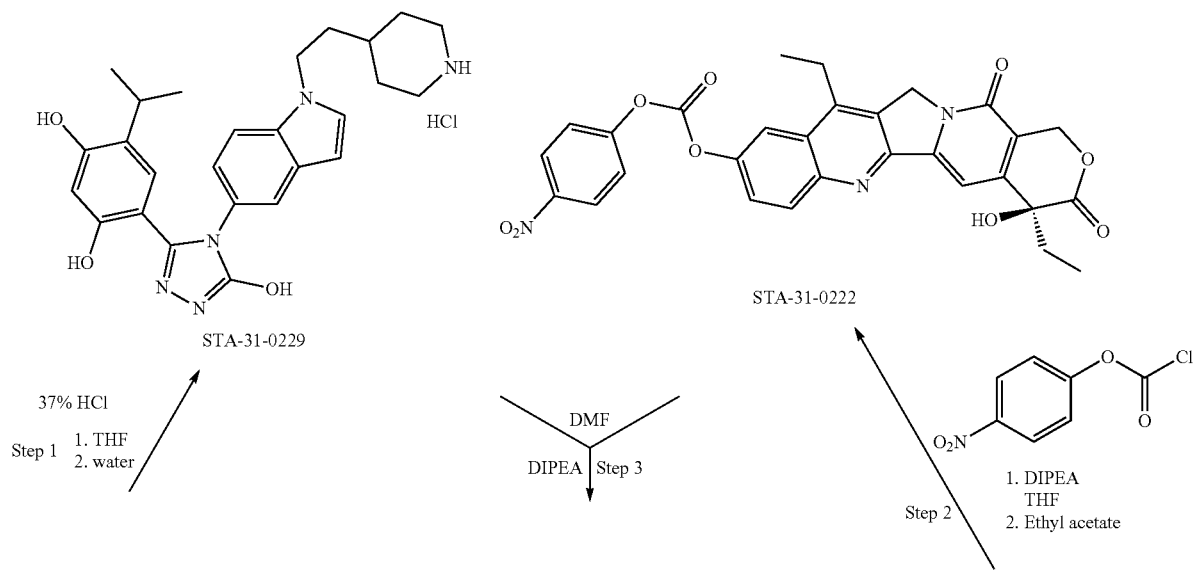

-continued

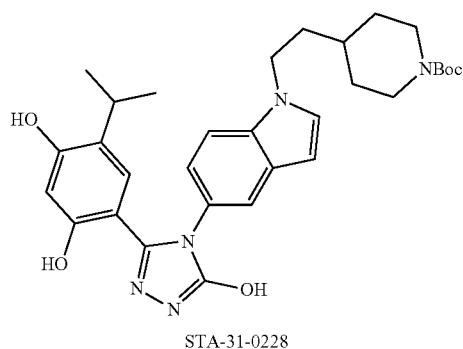

STA-31-0228

2M HCl | water

SDC-TRAP-0063 crude

Step4 | 1. DMSO, THF
2. Methanol
3. Water
4. SDC-TRAP-0063 seed crystals

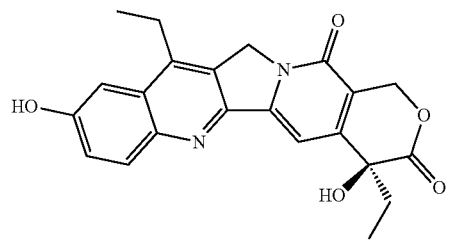

SN-38

SDC-TRAP-0063 once purified

Step 5 | 1. DMSO, THF
2. Methanol
3. Water
4. SDC-TRAP-0063 seed crystals

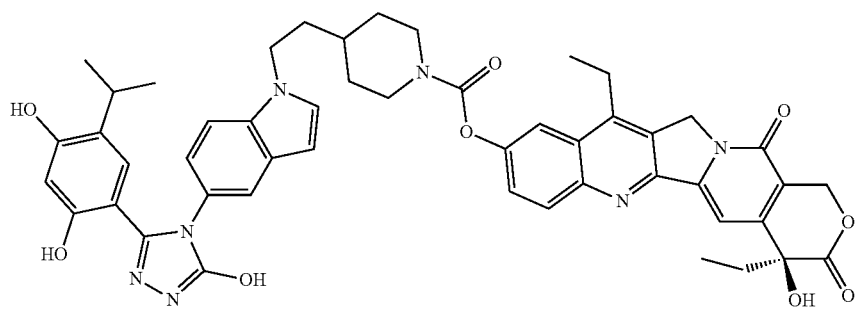

SDC-TRAP-0063

THF: Tetrahydrofuran
DIPEA: N,N-Diisopropylethylamine
DMF: N,N-dimethyl formamide
DMSO: Dimethyl sulfoxide Step 1, Manufacture of STA-31-0229

The manufacture of STA-31-0229 (4-(5-hydroxy-4-(1-(2-(piperidin-4-yl)ethyl)-1H-indol-5-yl)-4H-1,2,4-triazol-3-yl)-6-isopropylbenzene-1,3-diol hydrochloride) is described below.

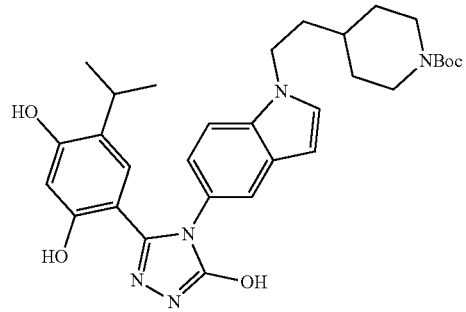

$C_{31}H_{39}N_5O_5$
M.W.: 561.68

STA-31-0228

37% HCl
1. THF
2. water

-continued

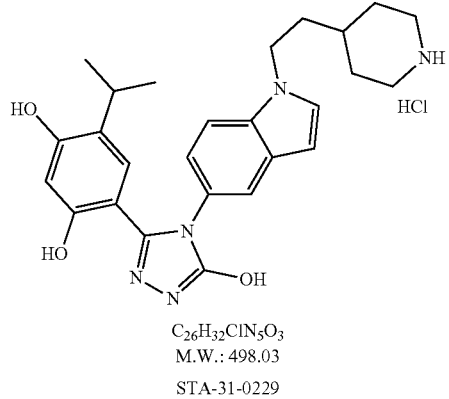

$C_{26}H_{32}ClN_5O_3$
M.W.: 498.03

STA-31-0229

STA-31-0228 (3.2 kg) and THF (11.7 kg) were charged to a reactor and stirred. Hydrochloric acid 37% (8.3 kg) was added to the stirred suspension slowly while maintaining the internal temperature at ≤40° C. The resulting mixture was stirred at ambient temperature for 2 hours and the completion of reaction was confirmed by HPLC. Water (64.1 kg) was added to the reaction mixture in portions, and the resulting suspension was stirred for about 17 hours to complete the precipitation. The solid was isolated by filtration, washed with water (48.7 kg) and dried under vacuum at a jacket temperature of about 60° C. to give STA-31-0229 (2.2 kg, 78% yield).

Step 2, Manufacture of STA-31-0222

The manufacture of STA-31-0222 ((S)-4,11-diethyl-4-hydroxy-3,14-dioxo-3,4,12,14-tetrahydro-1H-pyrano[3′,4′:6,7]indolizino[1,2-b]quinolin-9-yl (4-nitrophenyl) carbonate) is described below.

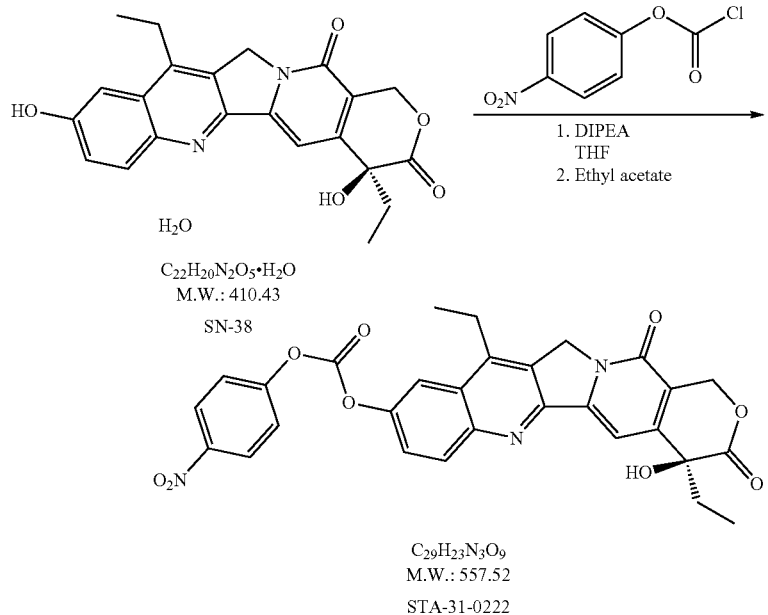

SN-38 (2.1 kg), THF (140.0 kg) and 4-nitrophenyl chloroformate (2.3 kg) were charged to a reactor and stirred. N,N-diisopropylethylamine (1.05 kg) was added to the reactor and the resulting mixture was stirred at ambient temperature for about 4 hours. A sample was pulled to monitor the completion of reaction by HPLC, ethyl acetate (48.0 kg) was added to the suspension, and stirring continued for about 4 hours. The solid was isolated by filtration, rinsed with ethyl acetate (25.3 kg) and dried under vacuum at a jacket temperature of about 50° C. to give STA-31-0222 (2.4 kg, 86% yield).

Step 3, Manufacture of SDC-TRAP-0063 Crude

The manufacture of SDC-TRAP-0063 crude is described below.

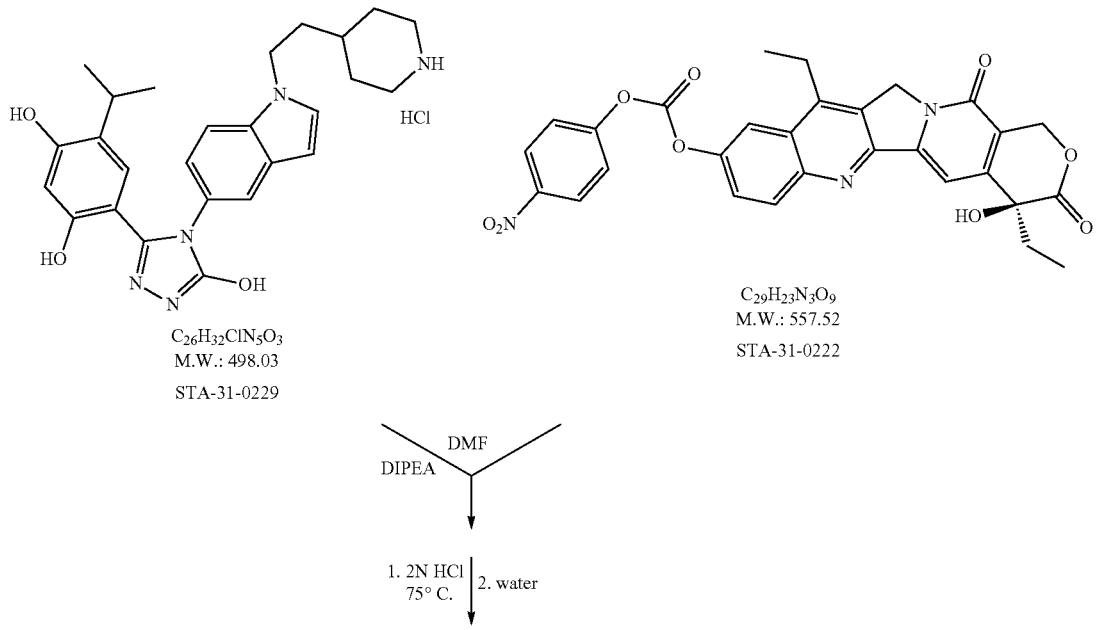

-continued

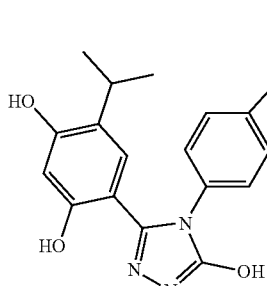 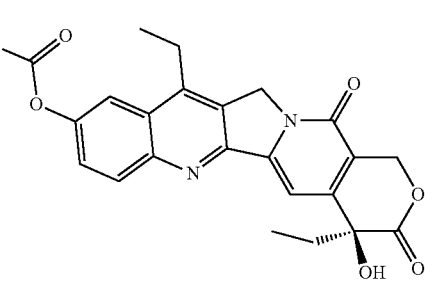

C₄₉H₄₉N₇O₉
M.W.: 879.95
SDC-TRAP-0063

STA-31-0229 (2.14 kg) and DMF (24.7 kg) were charged to a reactor and stirred. DIPEA (0.557 kg) was added to the reactor followed by a rinse with DMF (2.2 kg) and the resulting mixture was stirred for approximately 50 minutes. The mixture was cooled to about −10° C. Then STA-31-0222 (2.23 kg) and DMF (10.0 kg) were added. The resulting mixture was stirred for 1 hour at about −10° C. and the completion of reaction was confirmed by HPLC. 2N hydrochloric acid (7.75 kg) was added to the reaction mixture and the mixture was heated to about 60° C. 2N hydrochloric acid (12.9 kg) was added to the mixture, the contents were heated at about 75° C. for 6 hours to hydrolyze impurities RRT 1.19 and RRT 1.34, and removal of these impurities was confirmed by HPLC. Water (71.8 L) was charged to a separate reactor and stirred. The reaction mixture was cooled to about 60° C. and added to the water to precipitate SDC-TRAP-0063. The reactor was rinsed with DMF (7.4 kg) and the rinse was transferred to the precipitation mixture. The precipitated solid was isolated by filtration, washed with water (84.9 L), then with ethyl acetate (54.6 kg) and dried under vacuum at a jacket temperature of about 50° C. to give SDC-TRAP-0063 crude (3.2 kg, 91% yield).

Step 4, Manufacture of SDC-TRAP-0063 Once Purified

The manufacture of SDC-TRAP-0063 once purified in described below.

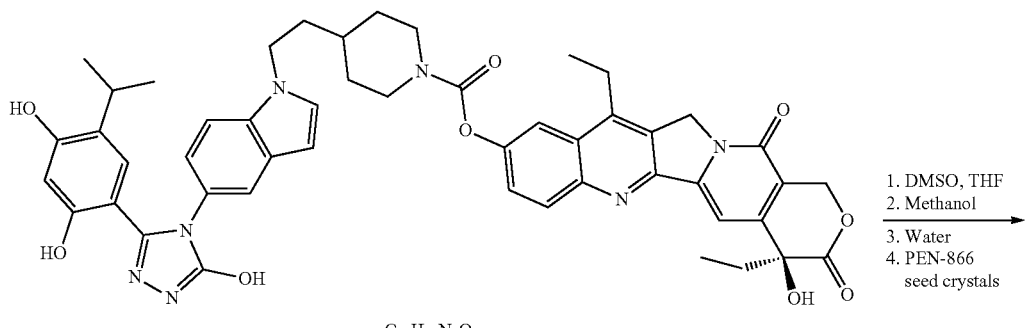

C₄₉H₄₉N₇O₉
M.W.: 879.95
SDC-TRAP-0063 crude

1. DMSO, THF
2. Methanol
3. Water
4. PEN-866 seed crystals

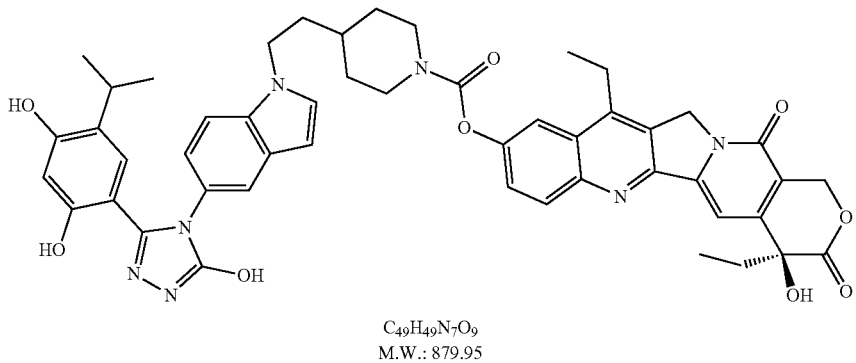

C₄₉H₄₉N₇O₉
M.W.: 879.95
SDC-TRAP-0063 once purified

DMSO (6.9 kg), THF (53.1 kg) and SDC-TRAP-0063 crude (3.19 kg) were charged to a reactor and stirred until a clear solution was formed. Methanol (9.7 kg) was added to the resulting solution. Water (57.5 kg) was slowly added to the resulting solution, followed by SDC-TRAP-0063 seed crystals (6.4 g) in water (64.3 g). The resulting mixture was stirred for about 2 hours to give a suspension. Water (9.8 kg) was added to the suspension and the mixture was stirred for approximately 16 hours at about 20° C. The solid was isolated by filtration, washed with water (12.9 L) and dried under vacuum at a jacket temperature of about 50° C. to give SDC-TRAP-0063 once purified (2.82 kg, 88% yield).

Step 5, Manufacture of SDC-TRAP-0063

The manufacture of SDC-TRAP-0063 is described below.

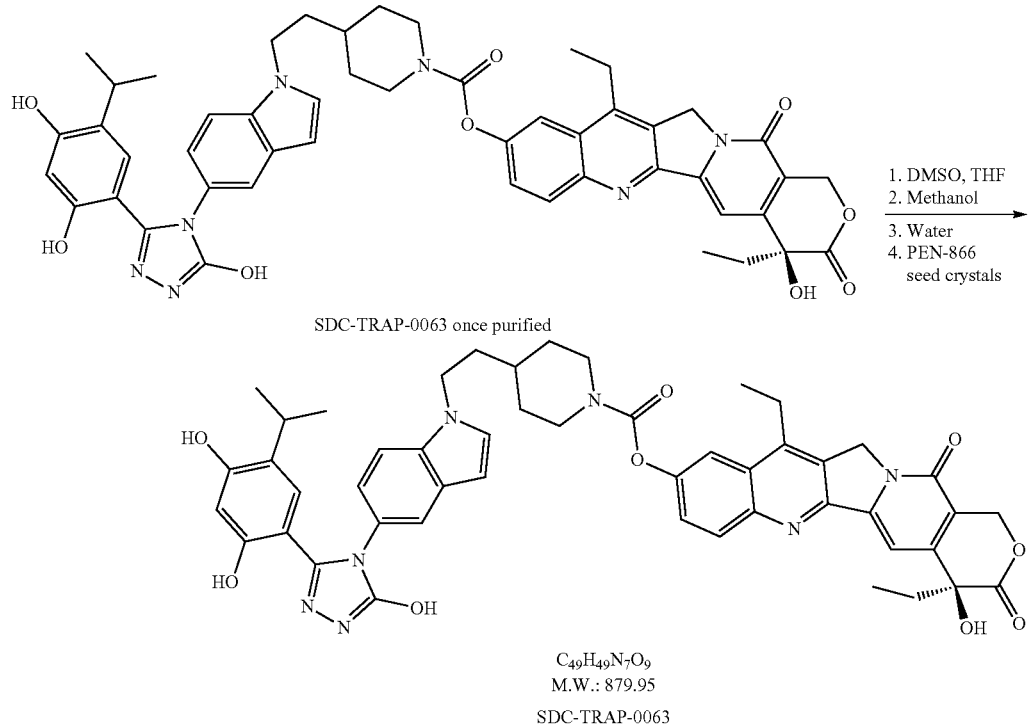

DMSO (5.6 kg), THF (45.2 kg) and SDC-TRAP-0063 once purified (2.82 kg) were charged to a reactor and stirred until a clear solution was formed. Methanol (8.5 kg) was added to the resulting solution, which was then transferred to another reactor through a polishing filter (0.2 µm), followed by a rinse with the same solvent mixture (2.97 kg). Water (47.8 kg) was slowly added through a polishing filter to the resulting solution, followed by SDC-TRAP-0063 seed crystals (5.7 g) in water (56.9 g). The resulting mixture was stirred for about 2.5 hours to give a suspension. Water (5.6 kg), filtered on a polishing filter, was added to the suspension and the mixture was stirred for approximately 16 hours at about 20° C. The solid was isolated by filtration, washed with water (16.8 L) and dried under vacuum at a jacket temperature of about 50° C. to give SDC-TRAP-0063 (2.42 kg, 86% yield).

In summary, the process of producing SDC-TRAP-0063 comprising the steps of:

1). synthesizing STA-31-0229 from STA-31-0228;

2). synthesizing STA-31-0222 from SN-38;

3). synthesizing SDC-TRAP-0063 Crude from STA-31-0229 and STA-31-0222; and

4). purifying SDC-TRAP-0063 Crude.

Example 2: Formulation of SDC-TRAP-0063

The prevent application provide pharmaceutical formulations or compositions comprising SDC-TRAP-0063 or derivatives or salts thereof. Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutical composition comprises tert-butanol as an excipient.

In some embodiments, the pharmaceutical composition comprises sodium chloride as an excipient.

In some embodiments, the pharmaceutical composition comprises water. SDC-TRAP-0063 or its derivatives or salts thereof may have a concentration of between about 50 to about 100 mg/mL.

Sodium Salt Derivative of SDC-TRAP-0063

In solution, SDC-TRAP-0063 contains a lactone ring at pH-dependent equilibrium with the corresponding open chain carboxylic acid form. At high pH (above pH of 9.3, pKa value) the equilibrium shifts toward an open ring carboxylic acid form and at low pH it shifts toward the closed ring lactone form.

The sodium salt (SDC-TRAP-0063 Sodium or SDC-TRAP-0063 Na) of the carboxylic acid derivative has a structure of

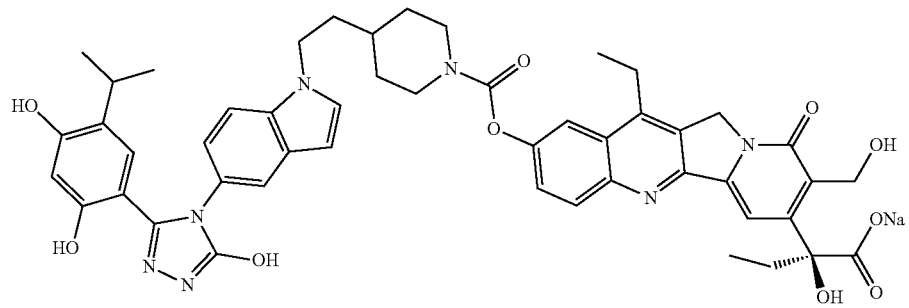

(Sodium (S)-2-(2-((4-(2-(5-(3-(2,4-dihydroxy-5-isopropylphenyl)-5-hydroxy-4H-1,2,4-triazol-4-yl)-1H-indol-1-yl)ethyl)piperidine-1-carbonyl)oxy)-12-ethyl-8-(hydroxymethyl)-9-oxo-9,11-dihydroindolizino[1,2-b]quinolin-7-yl)-2-hydroxybutanoate) or its tautomer:

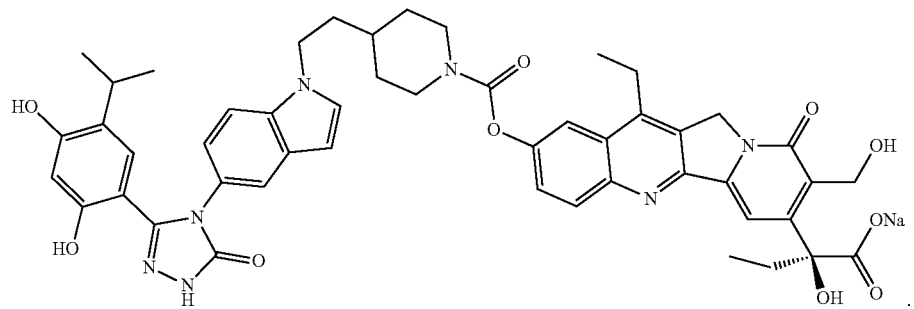

Structure of SDC-TRAP-0063 in both lactone and sodium salt form:

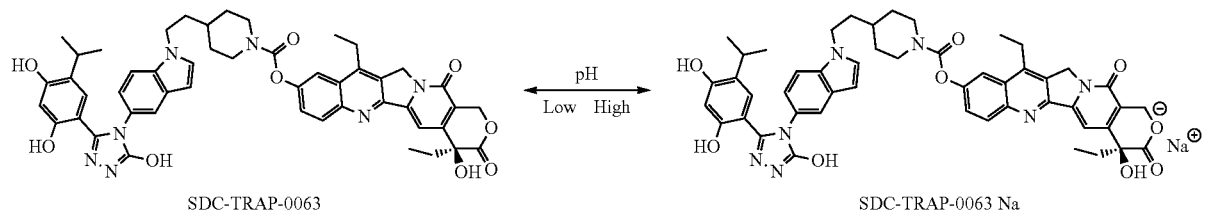

SDC-TRAP-0063 drug substance is isolated and stored in the lactone form and SDC-TRAP-0063 Sodium drug product is converted and stored in the carboxylic acid sodium salt form.

The flow diagram for the manufacturing processes and process control of SDC-TRAP-0063 Sodium is presented in FIG. 1. During the manufacturing process, SDC-TRAP-0063 was converted to SDC-TRAP-0063 Sodium, which is the dominant form at pH above 9.3. First, tert-butanol was melted at 25-30° C. and dispensed into a 2 liter glass mixing vessel jacketed at 25-30° C. The SDC-TRAP-0063 powder was added slowly into the stirring tert-butanol and mixed for at least 20 minutes with a ~2″ magnetic stir bar to adequately wet and suspend it. 0.3 normal aqueous sodium hydroxide solution is then slowly added and allowed to mix for at least an additional 1 hour. Complete dissolution of the SDC-TRAP-0063 powder was confirmed by visual observation while mixing. Water for Injection was then dispensed up to ~95% of the target total batch volume and mixed for 5 minutes. A sample was taken and measured to ensure pH was greater than or equal to 9.8, with option to adjust by incremental addition of up to two 1 milliliter aliquots of 0.3 normal aqueous sodium hydroxide solution if necessary. Water for Injection was again added to weight quantity sufficient (QS) and mixed for 5 minutes to complete compounding of the bulk drug solution. The 2 liter glass mixing vessel jacket temperature was then reduced to within 20-25° C. Product sterilization was achieved by filtration through at least two Millipore Opticap XL3 0.2 µm filters in series, and samples were taken immediately pre-filter for microbial enumeration testing. Depyrogenated 10 milliliter nominal size borosilicate glass vials are then aseptically filled with 1.1 milliliters of bulk drug solution per vial. Vials were stoppered into the lyophilization position, and loaded into a lyophilizer. Vials were lyophilized per the recipe in Table 1, and fully stoppered. Vials were aseptically removed from the lyophilizer and caps were crimped to seal the vials. Exterior vial washing and visual inspection were conducted to complete production of SDC-TRAP-0063 sodium in its primary enclosure.

TABLE 1

Lyophilization steps and conditions

| Step | Step Description | Temperature | Pressure | Duration |
|---|---|---|---|---|
| 1 | Loading | 5° C. | Atmospheric | Not applicable |
| 2 | Freezing | 5° C. | Atmospheric | 120 minutes |
| 3 | Freezing ramp | 5° C. to −50° C. | Atmospheric | 120 minutes |
| 4 | Freezing | −50° C. | Atmospheric | 210 minutes |
| 5 | Freezing ramp | −50° C. to −40° C. | Atmospheric | 15 minutes |
| 6 | Evacuation | −40° C. | 80 µbar | Not applicable |
| 7 | Primary drying ramp | −40° C. to −15° C. | 80 µbar | 50 minutes |
| 8 | Primary drying | −15° C. | 80 µbar | 1,260 minutes |
| 9 | Secondary drying ramp | −15° C. to 25° C. | 80 µbar | 156 minutes |
| 10 | Secondary drying | 25° C. | 80 µbar | 960 minutes |
| 11 | Pre-aeration with nitrogen | 25° C. | 800 µbar | Not applicable |
| 12 | Stoppering | 25° C. | 800 µbar | Not applicable |
| 13 | Aeration with nitrogen | 25° C. | Atmospheric | Not applicable |
| 14 | Unloading* | 25° C. | Atmospheric | Not applicable |

* If unloading is not immediate, maintain the shelves at 5 C.; before starting unloading, move the shelf temperature to the unloading temperature In summary, SDC-TRAP-0063 was completely dissolved in the co-solvent system of tert-butanol and 0.3N sodium hydroxide. Complete dissolution was confirmed visually. Water for Injection (WFI) was added to weight QS, and pH verification was then conducted with option to adjust pH if necessary. Sterile filtration was achieved with at least two 0.2 µm filters in series, followed by aseptic vial filling, partial stoppering, lyophilization, vial capping, and vial exterior wash.

The process of producing SDC-TRAP-0063 Sodium comprising the steps of:
1). dissolving SDC-TRAP-0063 in tert-butanol at 25-35° C.;
2). adding 0.3 normal aqueous sodium hydroxide and Water for Injection to adjust pH to be above around 9.8;
3). filtering the mixture from step 2). with at least two 0.2 µm filters in series; and
4). conducting aseptic vial filling and lyophilization.

Therefore, SDC-TRAP-0063 Sodium drug product was aseptically manufactured as a sterile-filtered solution that was lyophilized. The composition of the lyophilized drug product is shown below:

| Ingredient | Role | Amount (mg/vial) |
|---|---|---|
| SDC-TRAP-0063 sodium | Active | 105 |

This solution is filled to deliver 105 mg/vial into a container closure system consisting of a USP Type 1 clear glass vial, stopper, and overseal. The drug product is stored at 2° C. to 8° C., away from light. Prior to administration the lyophilized powder is reconstituted with Water for Injection and then is further diluted in 0.9% Sodium Chloride Injection, USP to the target concentration prior to use. SDC-TRAP-0063 Sodium may have a concentration of between about 25 to about 50 mg/mL, between about 50 to about 100 mg/mL, between about 100 to about 150 mg/mL, or between about 150 to about 200 mg/mL. The drug product is intended for intravenous administration by infusion.

The reconstituted solution of SDC-TRAP-0063 Sodium has a pH of 10.0. This solution is diluted to the target dose in 0.9% sodium chloride injection, USP. The pH of the infusion solution depends on the concentration of SDC-TRAP-0063 Sodium in the diluted infusion solution. Across the dose ranges employed in the clinical study protocol, the volume of the diluted infusion solution administered will range from 50 to 500 mL, and the pH will range from 8.1 to 9.6. In order to reduce the potential risks of injection site pain and/or damage to the venous endothelium during IV administration, a central venous access line is used for administration of the diluted SDC-TRAP-0063 Sodium.

The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

We claim:

1. A process of producing SDC-TRAP-0063 Sodium

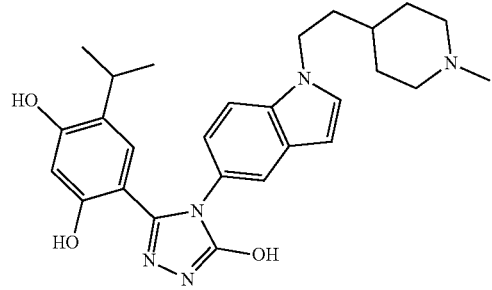

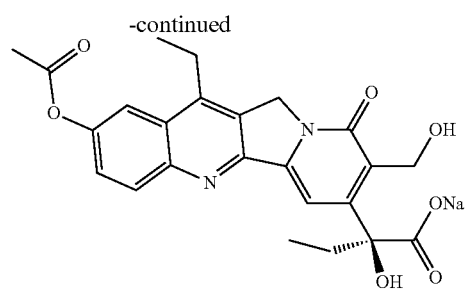

or its tautomer comprising the steps of:
1). dissolving SDC-TRAP-0063 in tert-butanol at 25-35° C.;
2). adding 0.3 normal aqueous sodium hydroxide and Water for Injection to adjust pH to be above around 9.8;
3). filtering the mixture from step 2). with at least two 0.2 μm filters in series; and
4). conducting aseptic vial filling and lyophilization.

* * * * *